(12) United States Patent
Aso et al.

(10) Patent No.: US 10,012,649 B2
(45) Date of Patent: Jul. 3, 2018

(54) DETECTION METHOD OF MAMMARY GLAND DISEASE

(71) Applicant: TOHOKU UNIVERSITY, Sendai-shi, Miyagi (JP)

(72) Inventors: Hisashi Aso, Sendai (JP); Haruki Kitazawa, Sendai (JP); Koichi Watanabe, Sendai (JP); Shuichi Owada, Sendai (JP); Hitoshi Watanabe, Sendai (JP); Yuya Nagasawa, Sendai (JP); Shunsuke Someya, Sendai (JP); Yoriko Horikoshi, Sendai (JP); Nanami Itaya, Sendai (JP)

(73) Assignee: TOHOKU UNIVERSITY, Sendai-Shi, Miyagi (JP)

( * ) Notice: Subject to any disclaimer, the term of this patent is extended or adjusted under 35 U.S.C. 154(b) by 101 days.

(21) Appl. No.: 14/413,855

(22) PCT Filed: Feb. 8, 2013

(86) PCT No.: PCT/JP2013/052955
§ 371 (c)(1),
(2) Date: Jan. 9, 2015

(87) PCT Pub. No.: WO2014/010261
PCT Pub. Date: Jan. 16, 2014

(65) Prior Publication Data
US 2015/0192585 A1   Jul. 9, 2015

(30) Foreign Application Priority Data
Jul. 12, 2012 (JP) ................. 2012-156163

(51) Int. Cl.
*G01N 33/573* (2006.01)
*G01N 33/68* (2006.01)
*C07K 16/40* (2006.01)

(52) U.S. Cl.
CPC ........... *G01N 33/573* (2013.01); *C07K 16/40* (2013.01); *G01N 33/6893* (2013.01); *G01N 2333/99* (2013.01); *G01N 2800/365* (2013.01)

(58) Field of Classification Search
None
See application file for complete search history.

(56) References Cited

U.S. PATENT DOCUMENTS

| | | | |
|---|---|---|---|
| 2007/0032423 A1* | 2/2007 | Clevenger .............. | A61K 38/52 514/11.3 |
| 2011/0207156 A1* | 8/2011 | Duncan ............. | G01N 33/57415 435/7.92 |
| 2015/0192585 A1* | 7/2015 | Aso ..................... | G01N 33/6893 435/7.4 |

FOREIGN PATENT DOCUMENTS

WO     WO 2014/010261 A1 *   1/2014

OTHER PUBLICATIONS

Hondo et al, Cell and Tissue Research, 2016, 364/3:585-597.*
Takanashi et al, Vet. Research, 2015, 46:80/1-80/10.*
Hillerton et al, J. Applied Microbiology, 2005, 98:1250-1255.*
Hillerton et al, J. Dairy Science, 2002, 85:1009-1014.*
Wilson et al, Journal of Dairy Science, Aug. 1999, 82/8:1664-1670 Abstract only.*
Arnold, Cooperative Extension Service, 2012.*
Ruegg, Responsible Use of Antibiotics for Treatment of Clinical Mastitis, eXtension, 2015 articles.extension.org/pages/72958/responsible-use-of-antibiotics-for-treatment-of-clinical-mastitis.*
Allain et al., "Selective assay for CyPA and CyPB in human blood using highly specific anti-peptide antibodies," Journal of Immunological Methods (1995), vol. 178, pp. 113-120.
Arora et al., "Extracellular Cyclophilins Contribute to the Regulation of Inflammatory Responses," The Journal of Immunology (2005), vol. 175, pp. 517-522.
Asai et al., "Predominant subpopulations of T lymphocytes in the mammary glad secretions during lactation and intraepithelial T lymphocytes in the intestine of dairy cows," Veterinary Immunology and Immunopathology (2000), vol. 73, pp. 233-240.
Asai et al., "Variation in CD4+ T and CD8+ T lymphocyte subpopulations in bovine mammary gland secretions during lactating and non-lactating periods," Veterinary Immunology and Immunopathology (1998), vol. 65, pp. 51-61.
Dosogne et al.; "Potential mechanism of action of J5 vaccine in protection against severe bovine coliform mastitis," Vet. Res. (2002), vol. 33, pp. 1-12.
Gronlund et al., "Changes in blood and milk lymphocyte subpopulations during acute and chronic phases of *Staphylococcus aureus* induced bovine mastitis," Research in Veterinary Science (2006), vol. 80, pp. 147-154.
Gwinn et al., "Novel Approach to Inhibit Asthma-Mediated Lung Inflammation Using Anti-CD147 Intervention," The Journal of Immunology (2006), vol. 177, pp. 4870-4879.
Handschumacher et al., "Cyclophilin: A Specific Cytosolic Binding Protein for Cyclosporin A," Science (1984), vol. 226, No. 4674, pp. 544-547.
Jin et al., "Cyclophilin A is a Secreted Growth Factor Induced by Oxidative Stress," Circ. Res. (2000), vol. 87, pp. 789-796.
Klastrup, N. O., "Bovine mastitis. Definition and guidelines for diagnosis," Kieler Milchwirtshaftliche Forschungsberichte (1985), vol. 37, No. 3, pp. 254-260.

(Continued)

*Primary Examiner* — Nita M. Minnifield
(74) *Attorney, Agent, or Firm* — Birch, Stewart, Kolasch & Birch, LLP

(57) ABSTRACT

The object of the present invention is to provide an early mastitis detection method that can detect mastitis easily and quickly when compared to the prior methods and also a biomarker to be used with the method.
The object can be solved by a method of examining a mammary gland disease by using the level of cyclophilin A in a mammary gland or in milk as indicator. More specifically, the object can be a method of examining a mammary gland disease comprising steps (1) and (2) listed below;
(1) a step of detecting cyclophilin A in the milk collected from an udder or an udder quarter of a subject and thereby determining the cyclophilin A level in the milk; and
(2) a step of determining the onset of a mammary gland disease or the possibility of onset of a mammary gland disease in the udder or the udder quarter of the subject on the basis of the cyclophilin A level in the milk.

3 Claims, 15 Drawing Sheets

(56) References Cited

OTHER PUBLICATIONS

Merle et al., "Cell function in the bovine mammary glad: a preliminary study on interdependence of healthy and infected udder quarters," Journal of Dairy Research (2007), vol. 74, pp. 174-179.

Riollet et al., "Cell Subpopulation and Cytokine Expression in Cow Milk in Response to Chronic *Staphylococcus aureus* infections," J. Dairy Sci. (2001), vol. 84, pp. 1077-1084.

Rivas et al., "Longitudinal evaluation of bovine mammary gland health status by somatic cell counting, flow cytometry, and cytology," J. Vet. Diagn. Invest. (2001), vol. 13, pp. 399-407.

Saphire et al., "Host cyclophilin A mediates HIV-1 attachment to target cells via heparans," The EMBO Journal (1999), vol. 18, No. 23, pp. 6771-6785.

Satoh et al., "Cyclophilin A enhances vascular oxidative stress and the development of angiotensin II-induced aortic aneurysms," Nature Medicine (Jun. 2009), vol. 15, No. 6, pp. 649-657.

Seko et al., "Hypoxia followed by reoxygenation induces secretion of cyclophiln A from cultured rat cardiac myocytes," Biochemical and Biophysical Research Communications (2004), vol. 317, pp. 162-168.

Sherry et al., "Identification of cyclophilin as a proinflammatory secretory product of lipopolysaccharide-activated macrophages," Proc. Natl. Acad. Sci. USA (Apr. 1992), vol. 89, pp. 3511-3515.

Wang, P. and J. Heitman, "The cyclophilins," Genome Biology (2005), vol. 6, pp. 226.1-226.6.

Xu et al., "Leukocyte Chemotactic Activity of Cyclophilin," The Journal of Biological Chemistry (Jun. 15, 1992), vol. 267, No. 17, pp. 11968-11971.

Yamaguchi et al., "A Phenotype of Mammary Intra-Epithelial Lymphocytes (mIEL) in Cows," Acta. Histochem. Cytochem. (2000), vol. 33, No. 1, pp. 11-15.

Yurchenko et al., "CD147 is a Signaling Receptor for Cyclophilin B," Biochemical and Biophysical Research Communications (2001), vol. 288, pp. 786-788.

"VII29-33 Lymphocyte chemotactc factor cyclophilin A confirmed in mammary gland tissues and milk in initital stages of mastitis," Japanese Society of Animal Science, the 115th event, Feb. 27, 2012, p. 233, Abstract, with English translation.

\* cited by examiner

DETECTION METHOD OF MAMMARY GLAND DISEASE

The present application claims the benefit of priority of Japanese Patent Application No. 2012-156163, filed on Jul. 12, 2012, the entire contents of which are incorporated herein by reference.

TECHNICAL FIELD

The present invention relates to the detection method of mammary gland disease such as mastitis in the udder or in one or more of quarter parts of udder.

BACKGROUND ART

The cow udder is divided into the left and the right by a thick medial suspensory ligament, and also into the front and the rear by thin membranes that operate as partition wall to constitute independent quarters. The cow udder contains a large number of mammary alveoli, and a single layer of mammary epithelial cells is arranged at the mammary gland side of each mammary alveolus. Mammary epithelial cells of a healthy cow are tightly connected by inter-cellular adhesion molecules such as tight junctions. Mammary epithelial cells form a layer, which functions as barrier for physically separating the inside and the outside of each of the mammary glands. The layer containing mammary epithelial cells prevents flowing substances from blood to milk or from milk to blood, and thus prevents the mutual influx of substances between milk and blood.

Mammary epithelial cells mainly bear (1) a function of synthesizing milk proteins and lactose and secreting them to the alveolar lumen of the mammary glands, (2) a function of transferring lipid droplets to the apical site of epithelial cells and projection of them on the cell surface to secret butterfat into the alveolar lumen and (3) a function of transferring serum albumin and immunoglobulin from blood into milk.

Generally, epithelial cells of skin and mucous membrane are involved in the defense mechanism of preventing the invasion of foreign objects, such as pathogenic microorganisms, to living bodies. Epithelial cells not only physically prevent invasions of pathogens into living bodies but also chemically inhibit invasions and proliferations of pathogenic microorganisms by lactic acid, mucin, lysozyme, antibacterial peptide and so on that epithelial cells produce. Epithelial cells are also involved in inducing early immune reactions by producing various cytokines, in addition to the above physical and chemical barriers.

On the fluctuations of appearance of leukocytes and mammary epithelial cells in milk, CD4+T cells that induce production of antibodies are mainly contained at dry periods, whereas cytotoxic γδ+T cells and CD8+T cells are mainly contained at lactation periods. In contrast, B cells and antibody producing cells that are involved in humoral immunity are practically contained in milk (see Non-Patent Documents 1 through 3 listed below, the contents of which are incorporated herein by reference for the purpose of supporting the disclosure of the present invention). Macrophages (Mφ), dendritic cells (DC), granulocytes are involved in the elimination mechanism of infected epithelial cells. In addition to the phagocytic cells, it has been reported that γδ+T cells and CD8+T are involved actively in cell-mediated immunity at lactation periods (see Non-Patent Documents 4 listed below, the contents of which are incorporated herein by reference for the purpose of supporting the disclosure of the present invention). Therefore, a considerable attention is attracted in a natural immunity for the immune system of mammary gland, unlike other organs where IgA is immediately produced by B cells, such as a intestinal mucosal immune system (see Non-Patent Documents 5 and 6 listed below, the contents of which are incorporated herein by reference for the purpose of supporting the disclosure of the present invention).

Mastitis is an inflammatory disease that is occurred after the invasion of pathogens into udders. After microorganisms such as bacteria, molds and enzymes invade an udder through the teat orifice of a mammary gland, the inflammation arises and then it develops mastitis in the mammary gland. An udder quarter with mastitis shows hypertrophy as a whole and the mammary tissue thereof is destroyed, if partly, when compared with a normal udder quarter. Symptoms of mastitis include (1) an increase in the number of somatic cells in the milk secreted from the infected udder quarter that arises as a result of mobilization of immune cells and (2) a fall in the quantity and quality of milk due to interstitial hypertrophy and atrophy of mammary alveoli. Individual cow suffering from mastitis can show general symptoms including appetite loss and diarrhea in addition to the above described symptoms and eventually die in some instances.

Mastitis is roughly divided into clinical mastitis and latent mastitis, which does not give rise to any clinical symptom but shows an increase in the number of somatic cells in milk. Latent mastitis is believed to be responsible for about 80% of the damage cost caused by mastitis. *Escherichia coli*, which is a Gram negative bacterium, causes serious inflammations which result in clinical mastitis, whereas Gram positive bacteria such as *Staphylococcus aureus* frequently cause latent mastitis. The frequency of clinical expressions of latent mastitis is relatively low, it is difficult to discover and medically treat latent mastitis. The problem is that the latent mastitis can spread among hosts of cows without being noticed. Additionally, latent mastitis can be aggravated to turn into clinical mastitis in some instances.

A major therapeutic method of mastitis is administration of antibiotic agent. However, when it comes to mastitis caused by *Staphylococcus aureus*, part of *Staphylococcus aureus* is resistant against antibiotic substances and can form minute abscesses in mammary glands to make it generally difficult to medically treat mastitis caused by *Staphylococcus aureus* by means of antibiotic agents.

Antibiotic agents are therapeutically effective in terms of prevention of infections. Since, however, administration of antibiotic agents is a symptomatic therapy, it cannot directly protect mammary gland tissues from damages. Other known therapeutic methods for mastitis include those employing physiologically active substances such as cytokines (GM-CSF, CXCL8, hIFN-α) and those employing natural substances showing anti-bacterial effects (Stevia extract fermentation products, defensins, BIMURON®), although some of them are still in experimental stages.

The PL test that employs changes in pH and in the viscosity in milk as indicators, which occur as a result of coagulation and denaturation due to the number of leucocytes in milk, is commonly utilized as a method of diagnosing mastitis. Additionally, there is the somatic cell count test method of using as indicator the number of immune cells released into milk due to the pathogenic bacteria that have invaded a mammary gland. Furthermore, the method of detecting as light the weak electric potential that appears when somatic cells are activated and using it as indicator, namely the chemical luminescence (CL) measurement method is also known (see Non-Patent Documents 14 listed below, the contents of which are incorporated herein by reference for the purpose of supporting the disclosure of the present invention). The CL measurement method is based on the principle of measuring the active oxygen release quantity of neutrophils by way of chemical luminescence. With regard to mastitis, some cases on fluctuations of lymphocyte subsets in milk have been reported, which are caused by the fact that immune cells such as lymphocytes that have reacted to bacteria in milk infiltrate in milk (see Non-Patent Documents 8 and 9 listed below, the contents of which are incorporated herein by reference for the purpose of supporting the disclosure of the present invention).

In immune responses to inflammations, migration and supply of leukocytes take an important role in the immunological monitoring of hosts in inflammations. Leukocyte migration is a phenomenon where leukocytes that have been stimulated by chemotactic factors such as chemokines, cytokines and physiologically active lipids, which are secreted during inflammation, infiltrate into tissues from blood vessels, move and accumulate to sites of inflammation. Various regulatory factors for leukocyte migrations are known. Among them, chemokines that belong to the chemotaxis factor cytokine family are mainly known. Other known factors include cyclophilins, which are one of chemotaxis factors. Cyclophilins appear in all cells of all living things including procaryotes and eucaryotes. Cyclophilins are generally intracellular proteins and show peptidyl-prolyl cis-trans-isomerase activity, which is a factor that is involved in folding of proteins. Cyclophilins are known as FK-506 binding proteins. Two of cyclophilins including 18 kDa cyclophilin A (CyPA) and 21 kDa cyclophilin B (CyPB) are dominant. Cyclophilin A is a cytoplasmic protein having no signal sequence, while cyclophilin B is linked to endoplasmic reticulum in the N-terminal signal sequence (see Non-Patent Documents 10 listed below, the contents of which are incorporated herein by reference for the purpose of supporting the disclosure of the present invention).

CyPA is a cyclophilin that exists most massively, and is believed to account for about 0.1 to 0.4% by quantity of the total intracellular proteins. CyPA is known as a member of the protein group belonging to the intracellular binding factors of cyclosporine A, which is an immunosuppressive agent (see Non-Patent Documents 11 and 12 listed below, the contents of which are incorporated herein by reference for the purpose of supporting the disclosure of the present invention). During the onset of inflammation, CyPA is also released and secreted from both dead cells and living cells and exerts its function outside cells (see Non-Patent Documents 13 through 16 listed below, the contents of which are incorporated herein by reference for the purpose of supporting the disclosure of the present invention). Particularly, CyPA that is secreted to the outside of cells causes migrations of leukocyte subsets such as monocytes, eosinophil granulocytes, neutrophils and T-lymphocytes (see Non-Patent Documents 13, 17 and 18 listed below, the contents of which are incorporated herein by reference for the purpose of supporting the disclosure of the present invention). Rises of CyPA levels in diseases such as sepsis, rheumatism, arthritis, pneumonia and aneurism have been reported (see Non-Patent Documents 19 and 20 listed below, the contents of which are incorporated herein by reference for the purpose of supporting the disclosure of the present invention). With regard to rheumatism, there are reports telling that the CyPA level and the number of neutrophils are correlated (see Non-Patent Documents 21 listed below, the contents of which are incorporated herein by reference for the purpose of supporting the disclosure of the present invention). Similarly, CyPA appears and are secreted in pulmonary epithelial cells and in vascular endothelial cells in some diseases including pneumonia and arterial aneurysm. Reports telling that extracellular CyPa is a powerful chemotaxis factor to monocytes, neutrophils, eocinophil granulocytes and T-lymphocytes of human are known (see Non-Patent Documents 21 listed below, the contents of which are incorporated herein by reference for the purpose of supporting the disclosure of the present invention). There are also known reports telling that CyPA can induce inflammations because it is released due to an acute inflammatory reaction such as mobilization of neutrophils when bacteria invade into living bodies (see Non-Patent Documents 11 listed below, the contents of which are incorporated herein by reference for the purpose of supporting the disclosure of the present invention).

PRIOR ART DOCUMENTS

Non-Patent Documents

Non-Patent Document 1: Asai et al. (1998) Vet. Immunol. Immunopathol. 65(11): 55-61
Non-Patent Document 2: Asai et al. (2000) Vet. Immunol. Immunopathol. 73(3-4): 233-240
Non-Patent Document 3: Dosogne et al. (2002) Vet. Res. 33(1): 1-12
Non-Patent Document 4: Yamaguchi et al. (2000) Acta Histochemicaet Cytochemica. 33(1): 11-15
Non-Patent Document 5: Ariel et al. (2001) J. Vet. Diagn. Invest. 13(5): 399-407
Non-Patent Document 6: Merle et al. (2007) J. Dairy. Res. 74: 174-179
Non-Patent Document 7: Hideyuki Takahashi et al. (2000) Agriculture, Forestry and Fishery Technologies Research Journal. 23(3): 20-24
Non-Patent Document 8: Riollet et al. (2001) J. Dairy. Sci. 84(5): 1077-1084
Non-Patent Document 9: Gronlund et al. (2006) Res. Vet. Sci. 80(2): 147-154
Non-Patent Document 10: Wang & Heitman. (2005) Genome. Biol. 6(7): 226
Non-Patent Document 11: Saphire et al. (1999) EMBO. J. 18: 6771-6785
Non-Patent Document 12: Handschumacher et al. (1984) Science. 226(4674): 544-547
Non-Patent Document 13: Sherry et al. (1992) Proc. Natl. Acad. Sci. 89(8): 3511-3515
Non-Patent Document 14: Allain et al. (1995) J. Immunol. Met. 178(1): 113-120
Non-Patent Document 15: Jin et al. (2000) Circ. Res. 87: 789-796
Non-Patent Document 16: Seko et al. (2004) Biochem. Biophys. Res. Commun. 317(1): 162-168
Non-Patent Document 17: Xu et al. (1992), J. Biol. Chem. 267: 11968-11971
Non-Patent Document 18: Yurchenko et al. (2001) Biochem. Biophys. Res. Commun. 288 (4): 786-788
Non-Patent Document 19: William et al. (2006) J. Immunol. 177(7): 4870-4879
Non-Patent Document 20: Satoh et al. (2009) Nat. Med. 15: 649-656
Non-Patent Document 21: Kamaplpreet et al. (2005) J. Immunol. 175(1): 517-522

DISCLOSURE OF THE INVENTION

Problems to be Solved by the Invention

Mastitis of livestock, in particular mastitis of cows, entails large economic losses. Such losses are caused not only by a reduced milk production level and an increase of therapeutic treatment expenses including expenses of antibiotics but also by disuse and death of infected cows resulting from development of mastitis. Mastitis is one of the most intractable diseases of livestock all over the world and the economic loss attributable to mastitis is estimated to be 80 billion yens per year in Japan and more than 1.8 billion dollars per year in the United State of America. Furthermore, as many therapeutic treatments of mastitis have been carried out with the use of antibiotics, menthicillin-resistant *Staphylococcus aureus* (MRSA) has been detected from the cow milk and the beef of mastitis-infected cows to give rise to a problem that MRSA can be propagated to human beings via such beef and milk.

Therefore, early detection and early treatment of mastitis is obviously vitally important to minimize the economic loss caused by mastitis. As an early mastitis treatment method, methods of administering natural substances including cytokines and anti-bacterial substances instead of antibiotics have been tried. However, such methods are still in experiment stages and have not been clinically utilized yet. Furthermore, clarification of the molecular mechanism of immune responses in mammary glands is required to realize early treatment of mastitis. However, the molecular mechanism still has many parts that are to be clarified. As the molecular mechanism of immune responses in mammary glands has not been satisfactorily clarified yet, the barrier that blocks realization of early treatment of mastitis is very huge. Therefore, there is a strong demand for early mastitis detection methods.

On the other hand, the PL test, which is the standard mastitis detection method at present, uses milk that has been already denatured and hence discharged from the subject cow that is in intermediate and late stages of mastitis. Therefore, the PL test lacks sensitivity necessary for early detection of mastitis. Thus, the CL activity measurement method seems to be promising for early detection of mastitis. However, since CL activity measurements require a special instrument, the CL activity measurement method is not suited for dairy farmers to use it on a daily basis, from the viewpoint of economy and availability. Thus, no mastitis detection method that every dairy farmer can practice easily and quickly on a daily basis is known to date.

Cyclophilin A accounts for about 0.1 to 0.4% by quantity of all the intracellular proteins and expressions thereof in pulmonary epithelial cells and vascular endothelial cells have been reported with regard to inflammations such as pneumonia and aneurism. However, there has not been any report on the use of cyclophilin A as biomarker for identifying sites of inflammation.

Therefore, one of the problems to be solved by the present invention is to provide an early mastitis detection method that can detect mastitis easily and quickly when compared to the prior methods and also a biomarker to be used with the method. Another problem to be solved by the present invention is to provide a kit to be used with the method, the components of the kit and substances that can be subjected to manufacture the components.

Means for Solving the Problems

The inventors of the present invention have made intensive research efforts of looking into the molecular mechanism of immune responses in mammary glands for the purpose of early detection and early treatment of mastitis. In the course of the research, the inventors paid attention to various cells and biological substances and conducted experiments on them on a trial and error basis to find out cells and biological substances that are effective for solving the above identified problems, although most of them were turned down as useless. For example, the inventors once focused their attention on several chemokines and cytokines only to find out that they are not effective for early detection and early treatment of mastitis. Eventually, the inventors came to focus their attention on cyclophilin A (CyPA).

CyPA expressions and their probability in mammary epithelial cells that develop mastitis are not known to date. However, the inventors of the present invention paid attention to the fact that in some tissues in living bodies, cells producing CyPA extracellularly release CyPA as leukocyte chemotactic factor at the time of occurrence of inflammation and can take a role in mobilizing immune cells to the site of inflammation. Furthermore, the inventors thought that clues for early detection of mastitis can be obtained by looking into the relationship between mastitis and CyPA. Thus, the inventors first looked into the level of expression of CyPA in mammary gland tissues that develop mastitis by means of immunocytochemical techniques. To the inventors' surprise, the inventors succeeded in finding that the level of expression of CyPA varies depending on the extent of progress of mastitis. Then, the inventors looked into the levels of expression of CyPA protein in milk samples originating from the udder quarters that develop mastitis by means of Western blotting techniques. To the inventors' further surprise, the inventors succeeded in finding the fact that the level of expression of CyPA in milk also varies depending on the extent of progress of mastitis. These results indicate that an udder quarter that develop mastitis can be identified by measuring the CyPA level in the mammary gland tissue of the udder quarter and in milk originating from the udder quarter. Furthermore, as the inventors in parallel conducted experiments on the PL method and the CL activity measurement method, which are known methods of identifying udder quarters that are infected by mastitis, the inventors succeeded in identifying an udder quarter that is in early stages of mastitis and hence cannot be identified by the known methods as udder quarter that either develops mastitis or has a possibility of developing mastitis. The present invention is completed on the basis of these findings and the above described successful experiments.

Thus, the present invention provides a method of examining a mammary gland disease by using the level of cyclophilin A in a mammary gland or in milk as indicator.

In another aspect of the present invention, there is provided a method of examining a mammary gland disease comprising steps (1) and (2) listed below;

(1) a step of detecting cyclophilin A in the milk collected from an udder or an udder quarter of a subject and thereby determining the cyclophilin A level in the milk; and (2) a step of determining the onset of a mammary gland disease or the possibility of onset of a mammary gland disease in the udder or the udder quarter of the subject on the basis of the cyclophilin A level in the milk.

Preferably, in the method of the present invention, the step (2) is a step of determining that the subject develops a mammary gland disease or has a possibility of onset of a mammary gland disease in the udder or the udder quarter when the cyclophilin A level in the milk is higher than the cyclophilin A level in the milk collected from a healthy udder or udder quarter.

Preferably, in the method of the present invention, the step (2) is a step of determining that the subject develops a mammary gland disease or has a possibility of onset of a mammary gland disease in the udder or the udder quarter when the cyclophilin A level in the milk is twice of or higher than twice of the cyclophilin A level in the milk collected from a healthy udder or udder quarter.

Instill another aspect of the present invention, there is provided a method of examining a mammary gland disease comprising steps (1') and (2') listed below;
(1') a step of detecting cyclophilin A in a mammary gland collected from an udder or an udder quarter of a subject and thereby determining the cyclophilin A level in the mammary gland; and
(2') a step of determining the onset of a mammary gland disease or the possibility of onset of a mammary gland disease in the udder or the udder quarter of the subject on the basis of the cyclophilin A level in the mammary gland.

Preferably, in the method of the present invention, the step (2') is a step of determining that the subject has the onset or a possibility of onset of a mammary gland disease in the udder or the udder quarter when the cyclophilin A level in the mammary gland is higher than the cyclophilin A level in the mammary gland collected from a healthy udder or udder quarter.

Preferably, in the method of the present invention, the mammary gland disease is an infectious mammary gland disease.

Preferably, in the method of the present invention, the mammary gland disease is mastitis.

Preferably, in the method of the present invention, the subject is a human being or an animal that is not a human being.

Preferably, in the method of the present invention, the animal that is not a human being is selected from a group consisting of bovines, goats, water buffaloes, yaks, sheep, horses and camels.

Preferably, in the method of the present invention, detecting cyclophilin A is carried out by a technique selected from a group consisting of Western blotting, enzyme-linked immunosorbent assay, enzyme immunometric assay (EIA), fluoroimmunoassay (FIA), radioimmunoassay (RIA), fluorescence polarization immunoassay, chemiluminescent immunoassay, chemiluminescentenzyme immunoassay, electrochemiluminescent immunoassay, ELISPOT assay, immunoprecipitation assay, precipitation reaction, gel diffusion precipitation reaction, coagulation immunoassay, latex coagulation and chromatography.

Instill another aspect of the present invention, there is provided a reagent for examining a mammary gland disease comprising anti-cyclophilin A antibody.

Preferably, in the reagent of the present invention, the anti-cyclophilin A antibody is bound to an insoluble carrier and immobilized.

Preferably, in the reagent of the present invention, the insoluble carrier is in the form of beads, plates or thin film.

Preferably, in the reagent of the present invention, the mammary gland disease is an infectious mammary gland disease.

Preferably, in the reagent of the present invention, the mammary gland disease is mastitis.

In still another aspect of the present invention, there is provided a kit for examining a mammary gland disease comprising the reagent of the present invention.

In still another aspect of the present invention, there is provided a hybridoma having an ability of producing anti-cyclophilin A antibody.

In still another aspect of the present invention, there is provided an anti-cyclophilin A antibody produced by the hybridoma of the present invention.

In a further aspect of the present invention, there is provided a marker for detecting a mammary gland disease comprising cyclophilin A.

Preferably, in the marker of the present invention, the mammary gland disease is an infectious mammary gland disease.

Preferably, in the marker of the present invention, the mammary gland disease is mastitis.

Advantages of the Invention

According to the method of the present invention, a site in a subject that is infected by a mammary gland disease can be identified easily and quickly if compared with any known comparable methods as a result of using as indicator the expression level of cyclophilin A in milk or in mammary gland tissue obtained from the subject. The method of the present invention is particularly effective for identifying an udder or an udder quarter that is in initial stages of mastitis. Additionally, since the method of the present invention is a non-invasive method, it is possibly applicable to prevention of mastitis.

Since the method of the present invention can be put to practice easily and quickly, the method enables onsite measurements in dairy farms. If it is possible to determine mastitis in an udder or an udder quarter in early stages of the disease, milking can be suspended early, a treatment can be started early with the use of a small amount of antibiotic agent, and the duration of infection can be curtailed and milking can be resumed early so that treatment expenses can be suppressed and the economic loss of the dairy farmer feeding the cow due to the reduction of income caused by a reduced amount of milk obtained by milking can be minimized.

Cows are most liable to be infected by mastitis in the postpartum period at and near the time point of a month after a baby birth. The infection rate is believed to be about 10%. If the onset of mastitis in a cow or the possibility thereof can be detected early, not only a mastitis treatment can be started early but also the disuse of the cow can be discussed early so that the economic loss attributable to the mastitis can be minimized in any event. Therefore, the method of the present invention can contribute to reduction of the economic loss of the entire dairy industry.

The kit of the present invention is for executing the method of the present invention and hence the existence level of cyclophilin A in the whey obtained by centrifugation of the milk collected from a subject can be determined easily and quickly on the basis of antigen-antibody reaction by means of the kit of the present invention. The hybridoma of the present invention is for preparing anti-cyclophilin A antibody to be subjected to the method of the present invention and/or the kit of the present invention and the antibody of the present invention is anti-cyclophilin A antibody itself. Therefore, both the hybridoma of the present invention and the antibody of the present invention can contribute to early detection of mastitis in an easy and quick way through the method and kit of the present invention. The marker of the present invention is a biomarker that operates excellently for early prediction of mastitis.

BRIEF DESCRIPTION OF THE DRAWINGS

In FIG. 8, the left side shows the results of analysis of proteins in milk subjected to a non-reducing treatment, whereas the right side shows the results of analysis of proteins in milk subjected to a reducing treatment. The arrow (→) in around 60 kDa shows how EgG of 160 kDa is reduced by a reducing treatment in analysis No. 9 for a inflammatory udder quarter. The arrow (→) in around 50 kDa indicates that band expression arises even when proteins are subjected to a reducing treatment.

FIG. 11 is a graph showing the CyPA expression intensity in milk obtained by using the analysis results of FIG. 10A through 10C with the use of the expression level of analysis No. 42 as reference in contrast with the CL activity. The figure proves that a correlation exists between the CL activity and the CyPA expression level in milk ($p<0.0001$). As for the numerals and the signs in the figure, the numerals are the respective analysis Nos. and "○" represents a sample where PL was negative and CL was $<1\times10^6$ cpm/ml, while "●" represents a sample where PL was positive and CL was $\leq 50\times10^6$ cpm/ml, and "□" represents a sample where PL was negative and CL ranged between $1\times10^6$ cpm/ml and $50\times10^6$ cpm/ml ($1\times10^6$ cpm/ml$<$CL$<50\times10^6$ cpm/ml).

MODES FOR CARRYING OUT THE INVENTION

Figure 1A:
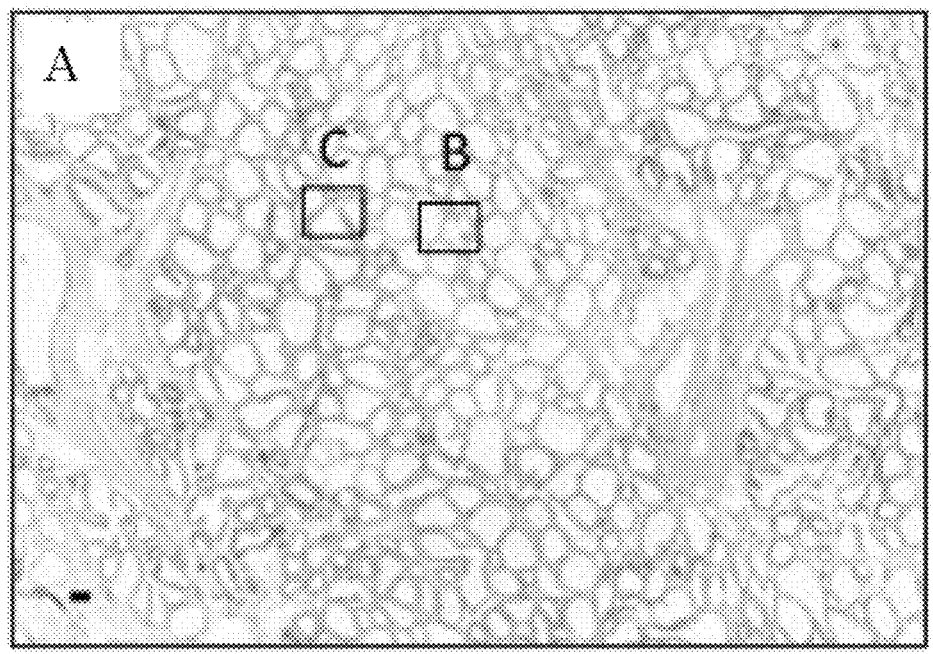
FIG. 1A is a picture illustrating localization of CyPA expression in a specimen of sliced mammary gland tissue in the mammary gland substratum prepared from a normal cow mammary gland of an SEC administration experimental mastitis district by immuno-staining with the use of anti-CyPA (2H5-F3 antibody). The figure proves that the mammary alveoli are large and the number of stromata is small in normal mammary gland tissues of cow. The bar in FIG. 1A is 500 µm long.

Hereinafter, the present invention will be described in detail.

1. Method of Examining a Mammary Gland Disease

The method of the present invention relates to a method of examining a mammary gland disease using the cyclophilin A level either in a mammary gland or in milk as indicator.

The object to be examined for the method of the present invention is a mammary gland disease. For the purpose of the present invention, mammary gland disease is an inclusive term including all pathological modes that give rise to abnormality in mammary glands in udders and udder quarters. Examples of mammary gland disease include infectious mammary gland diseases attributable to foreign objects such as bacteria and tumoral mammary gland diseases such as mammary cancer and fibroadenoma. While there are no particular limitations to mammary gland diseases to which the present invention is applicable, the present invention is preferably applied to infectious mammary gland diseases, more preferably to mastitis, because an increase in the cyclophilin A level is observed in mammary gland tissue where the onset of a mammary gland disease is recognized and milk secreted from such mammary gland tissue.

Mastitis is an inflammatory disease that occurs in an udder as a pathogen invades the udder. It is assumed that the onset of mastitis arises as (1) microorganisms including bacteria such as *Staphylococcus aureus* and *Escherichia coli*, mold and yeasts invades a mammary gland through a teat orifice to give rise to inflammation in the mammary gland and/or (2) bacterial toxins such as LPS and SEs produced from any of the above microorganisms, coagulase and some other protein remain fixed on mammary epithelial cells to cause inflammatory reactions to take place there.

Mastitis is roughly divided into clinical mastitis and latent mastitis. Clinical mastitis can be visually determined by observing the udder and the milk by naked eyes because symptoms such as swelling and heat are seen in the udder developing clinical mastitis, and denaturation including appearance of clots and increased viscosity is seen in the milk secreted from the udder. Latent mastitis, on the other hand, does not reveal such abnormalities and can be determined only by examining the milk produced from the udder in question. The milk examination has been carried out in the past by means of a method of detecting any pathogen in milk, a PL test (modified CMT method) based on an increase of the somatic cell count (SCC) in milk or a change in pH of milk and/or the CL activity measurement method of measuring the chemical luminescence activity (CL activity) in milk. However, the method of the present invention can be replaced or be used in parallel with any of the above-listed known methods that have been employed for milk examination. Therefore, the method of the present invention is further preferably to be applied to latent mastitis among different mammary gland diseases.

The method of the present invention can be utilized to determine not only the onset of a mammary gland disease including mastitis but also the possibility of onset of the mammary gland disease including the prediction of the risk of onset of the mammary gland disease and the early prediction of the mammary gland disease.

For the method of the present invention, the mammary gland that provides samples are not limited so long as it is within the scope of the meaning thereof normally used by those who are skilled in the art. Ordinarily, a mammary gland refers to a secretory gland found in an udder and having a function of secreting milk. In the mammary gland, a single layer of mammary epithelial cells is arranged at cavity side of each mammary alveolus and functions as physical barrier for separating the inside and the outside of the mammary alveolus. It is known that mammary epithelial cells produce various cytokines and anti-bacterial peptides. Additionally, mammarial intra-epithelial cell lymphocytes (mIEL) exist in the mammary gland. The samples provided from a mammary gland may not only include mammary gland tissue itself but also sites that form mammary gland tissue, e.g., mammary epithelial cells and other cells. As far as the method of the present invention is concerned, milk is not subjected to any limitations so long as it is within the scope of the meaning thereof normally used by those who are skilled in the art, although it may normally refer to a liquid substance secreted from mammary glands.

Cyclophilin A (CyPA) is a protein having peptidyl-prolyl cis-trans isomerase activity, which is a factor that is involved in protein folding. The molecular weight of CyPA is about 18 kDa. According to the data registered at GenBank that is a public data base of National Center for Biotechnology Information (NCBI), the amino acid sequence of CyPA is DAA30468 for bovine-derived ACCESSION, AAP03083 for sheep-derived ACCESSION, AAD50966 for mouse-derived ACCESSION, NP_001027981 for rhesus monkey-derived ACCESSION, ABB77876 for chimpanzee-derived ACCESSION, NP_058797 for rat-derived ACCESSION, NP_001126060 for orangutan-derived ACCESSION and NP_066953, NP_001008741 for human being-derived ACCESSION, which are indicated respectively as sequence Numbers 1 through 8 in the sequence listing. No gene information is registered for goat and horse to date. The method of the present invention is preferably employed to detect cyclophilin A that is derived from the subject to be examined for mammary gland diseases.

The cyclophilin A (CyPA) level to which the method of the present invention is applicable is not subjected to any particular limitations so long as the level of existence of CyPA is concerned. The CyPA level may be expressed by an absolute value and/or a relative value. The CyPA level may be determined physically, chemically and/or biologically. Thus, the method of the present invention is executed by using the CyPA level in a mammary gland or in milk as indicator without being restricted by any particular steps or processes. The method of the present invention does not use the CyPA level found in a living body as indicator but uses the CyPA level found in the mammary gland or the milk collected from a living body. Therefore, with regard to a marker according to the present invention, which will be described hereinafter, the CyPA isolated from the mammary gland or the milk collected from a living body is employed as marker for detecting a mammary gland disease.

In a mode of carrying out the present invention, there is provided a method of examining a mammary gland disease comprising steps (1) and (2) listed below;

(1) a step of detecting CyPA in the milk collected from an udder or an udder quarter of a subject and thereby determining the CyPA level in the milk; and (2) a step of determining the onset of a mammary gland disease or the possibility of onset of a mammary gland disease in the udder or the udder quarter of the subject on the basis of the CyPA level in the milk.

For the method of the present invention, there are no particular limitations to the subject and the subject may be human or non-human. The subject is preferably non-human because it is difficult to determine the possibility of onset of latent mastitis for a non-human subject. More preferably, the subject is a cow, a goat, a water buffalo, a yak, a sheep, a horse or a camel and further preferably the subject is a cow.

The udder contains lobes of mammary gland that are clots of in the mammary glands, and the milk that is produced in the mammary alveoli in the lobes is secreted to the outside of the body by way of the mammary duct from the teat. While the above described structure of udder is basically common to all animals, the structure varies from species to species. While human beings have a pair of breasts including the right breast and the left breast, the bovine udder is divided into four independent quarters; the left and the right by a thick medial suspensory ligament and also into the front and the rear by thin membranes as partition wall of quarters.

As far as the method of the present invention is concerned, while the udder and the udder quarters refer to those that are normally understood by those who are skilled in the art. For example, the human breast refers to one of the pair of breasts, the bovine udder quarter refers to one of the four independent udder quarters.

The method of collecting milk from an udder or an udder quarter of the subject is not concerned by any particular limitations. In other words, any means that those who are skilled in the art employ for may be normally adopted for the purpose of the present invention, which includes the means of milking from the udder at room temperature. The quantity of milk to be collected for the purpose of the present invention is not subjected to any particular limitations so long as it allows detection of CyPA. In other words, the quantity of milk to be collected for the purpose of the present invention can be made to be variable as a function of the means of detecting CyPA.

While the timing of collecting milk for the purpose of the present invention is not subjected to any particular limitations, it is preferable to serially or periodically collect milk from an udder or an udder quarter of a subject that is currently being milked or possibly milked so as to determine the possible onset of mastitis in an udder or an udder quarter of the subject in view of the fact that a rise of CyPA level is highly sensitively detected in the milk obtained from an udder quarter that shows the onset of mastitis and the fact that a rise of CyPA level is recognized in the milk obtained from an udder quarter that is suspected for mastitis. The possible onset of a mammary gland disease can be predicted early by using milk that is collected before or immediately after the start of an ordinary milking operation. In addition, from the viewpoint of early prediction of a mammary gland disease, it is preferable to select subjects whose udders or udder quarters do not provide any sign of onset of mastitis for diagnostic comparison.

There are no particular limitations to the technique of detecting CyPA. In other words, any of the techniques of detecting a particular protein, a particular polypeptide or a particular mRNA that are known to those who are skilled in the art may be applied to the present invention. In the present specification, the expression of "detecting cyclophilin A" is synonymous with "measuring the cyclophilin A level". While it is preferable to rigorously quantify the cyclophilin A level at the time of detecting Cyclophilin A, the cyclophilin A level may alternatively semi-quantitatively be measured for the purpose of the present invention. In other words, it is sufficient to detect the CyPA level to such an extent that allows comparison with the reference level to be compared. Examples of the techniques of detecting the CyPA for the purpose of the present invention may include a technique of separately executing two steps including a step of isolating CyPA and the following step of measuring the CyPA level for the isolated CyPA, and a technique of executing these steps as a single step.

At the time of detecting CyPA, it is preferable to subject the specimen containing CyPA to a reducing treatment. There are no particular limitations to the technique of subjecting the specimen containing CyPA to a reducing treatment and any appropriate one may be selected from the reducing treatment techniques known to those who are skilled in the art. Examples of known reducing treatment techniques include those using a reducing substance selected from reducing substances such as ascorbic acid, β-mercaptoethanol and dithiothreitol. Of these known techniques, a reducing treatment technique using β-mercaptoethanol is preferable for the purpose of the present invention.

With the method of the present invention, CyPA can be detected, for example, by means of an immunological technique such as Western blot assay, sandwich assay or competitive assay and also by means of a chromatography-based analytical and chemical technique such as high performance liquid chromatography and gel filtration chromatography due to acquire the profile of CyPA in advance. Techniques that can be employed to detect CyPA for the purpose of the present invention include, for example, Western blot assay, enzyme-linked immunosorbent assay, enzyme immunoassay (EIA), fluorescence immunoassay (FIA), radiation immunoassay (RIA), fluorescence polarization immunoassay, chemiluminescent immunoassay, chemiluminescent enzyme immunoassay, electrochemiluminescent immunoassay, ELISPOT assay, immunoprecipitation assay, precipitation reaction, gel diffusion precipitation reaction, coagulation immunoassay, latex coagulation and chromatography.

An immunological technique is preferably utilized as means of detecting CyPA for the method of the present invention. Immunological techniques include those that can measure the CyPA level immediately, easily and highly sensitively. Substances having specific affinity for CyPA such as anti-CyPA antibody are employed to detect the CyPA level by means of immunological techniques. Not only anti-CyPA antibody but also any of various substances having specific affinity for CyPA can be employed provided that the extents of binding of such substances relative to CyPA are measurable. For detection of CyPA, techniques of employing various steps such as steps of capturing and detecting an antigen may be applied in addition to techniques of directly detecting CyPA in the specimen by means of a labelled antibody.

Western blot assay is an example of techniques of detecting CyPA. Western blot assay is one of the techniques of separately executing separate steps for isolation and quantification of a target protein. While the Western blot assay to be used for detecting CyPA is not subjected to any particular limitations for the purpose of the present invention, an example of techniques as described below can be adopted. Firstly, out of the whey sample obtained by centrifugation of milk, CyPA is separated from the remaining proteins by SDS-PAGE. Then, the bands (protein) on the gel are transferred onto a membrane. Thereafter, the membrane is provided with anti-CyPA antibody. Subsequently, the membrane is provided with a labelled antibody against the anti-CyPA antibody. Finally, the quantity and the level of activity of the labelled substance of the band that corresponds to the CyPA on the membrane are measured.

However, the Western blot assay for detecting CyPA is not limited to the above described technique. For example, the labelled antibody against the anti-CyPA antibody may be enzyme-labelled or fluorescence-labelled. Various procedures and conditions relating to the Western blot assay may be appropriately modified by means of a technique known to those who are skilled in the art.

Immunological techniques for measuring the CyPA level rapidly, easily and highly sensitively include FIA and EIA. FIA employs a fluorescence-labelled antibody to detect an antigen-antibody complex (immunocomplex) by using fluorescence as signal (label). EIA employs an enzyme-labelled antibody to detect an immunocomplex by using color development or light emission based on an enzyme reaction as signal.

ELISA is a technique that is included in EIA. ELISA provides many advantages including a high detection sensitivity, a high specificity, an excellent quantizability, an easy operability, suitableness for simultaneous treatments of a large number of samples. ELISA includes competitive assay, sandwich assay and direct adsorption assay.

Competitive assay is a technique based on the principle of adding an antigen along with a sample and causing them to compete with each other for forming an immunocomplex. Sandwich assay is a technique that normally uses antibodies of two different types that are different in terms of epitope (a primary antibody that is an antibody for capturing and a secondary antibody for detection). While the procedures of these assays are summarily described below, these assays are by no means limited to the below-described procedures.

With competitive assay, the CyPA protein in a whey sample and the labelled CyPA protein are caused to competitively react with anti-CyPA antibody, then unreacted labelled CyPA (F) is separated from labelled CyPA (B) that is bonded to antibody (B/F separation), thereafter the labelled quantity of either B or F is measured to quantify the CyPA protein in the whey sample. For competitive assay, a liquid phase method of using soluble antibody as primary antibody and also using secondary antibody against polyethylene glycol or anti-CyPA antibody (primary antibody) for B/F separation, a direct immobilization method using an immobilized antibody as primary antibody and an indirect immobilization method using a soluble antibody as primary antibody and an immobilized antibody as secondary antibody are included, although there are no particular limitations to competitive assay to be employed.

With sandwich assay, a whey sample is made to react with a first anti-CyPA antibody that is immobilized to a carrier (primary reaction) and then made to react with a second anti-CyPA antibody that is labelled and can recognize a different epitope than that recognized by the first anti-CyPA antibody (secondary reaction). Subsequently, the quantity or the activity of the labelling agent on the carrier is measured. As for examples of sandwich assay, the primary reaction may be made to take place followed by the secondary reaction or, conversely, the secondary reaction may be made to take place followed by the primary reaction. Furthermore, the primary reaction and the secondary reaction may be made to take place simultaneously or with a time interval. The labelling agent to be used can be appropriately selected by those who are skilled in the art. As for the antibody immobilized to the carrier or the labelled antibody, a mixture of antibodies of two or more different types may be used in order to improve the sensitivity of measurement and/or for some other purposes.

A specific operation method for utilizing ELISA assay will be described below as an example. Firstly, anti-CyPA antibody is immobilized to an insoluble carrier. More specifically, for example, the surface of a micro-plate is sensitized (coated) with anti-CyPA antibody (primary antibody). Then, a sample obtained by centrifugation of milk or crushed mammary epithelial cells is brought into contact with the immobilized antibody. If antigen (CyPA) against the immobilized anti-CyPA antibody exists in the sample, an immunocomplex is formed as a result of this operation. After removing the non-specifically linked components by means of a cleaning operation, the immunocomplex is labelled by adding an enzyme-linked antibody (secondary antibody) and then the enzyme substrate is made to react with the immune complex for color development. Then, the immunocomplex is detected by using the extent of color development as indicator. ELISA assay is described in detail in many books and papers, which can be referred to when determining the experiment procedures of and the experiment conditions of each method.

When applying any of the above-described techniques of detecting CyPA to the method of the present invention, no particular setups that include specific conditions and operations which are beyond the state of the art are required. The CyPA protein measurement system may be constituted by adding ordinarily technical considerations given by those who are skilled in the art to the ordinary conditions and operations of any of the techniques. Details of these general technical means can be obtained by referring to general information manuals and books.

Examples of such general information manuals and books will be listed below. Eiji Ishikawa et al., "Enzyme Immunoassays" (Igakushoin, 1978), Eiji Ishikawa et al., "Enzyme Immunoassays" (2nd ed.) (Igakushoin 1982), Eiji Ishikawa et al., "Enzyme Immunoassays" (3rd ed.) (Igakushoin 1987), Hiroshi Irie "Radio Immunoassays" (Kodansha, 1974), Hiroshi Irie "Radio Immunoassays Part II" (Kodansha, 1979), "Methods in ENZYMOLOGY" Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: monoclonal Antibodies and General Immunoassay Methods)), ibid., Vol. 121 (Immunochemical Techniques (Part I: Hybridoma Technology and Monoclonal Antibodies)) (Academic Press) (the contents of which are incorporated herein by reference for the purpose of supporting the disclosure of the present invention).

With the method of the present invention, the onset of a mammary gland disease or the possible onset of a mammary gland disease in an udder or an udder quarter of the subject is determined on the basis of the cyclophilin A level (measured CyPA level) in the milk obtained by detecting cyclophilin A in the milk in Step (2). Determination of onset of a mammary gland disease or possible onset of a mammary gland disease may be done either qualitatively or quantitatively. Examples of qualitative determination and examples of quantitative determination are described below. Determinations described below may be made programmatically, automatically or mechanically without relying on the determination by those who are skilled in the art as may be clear from the criteria for determination.

As an embodiment of qualitative determination, it is determined that "there is the onset of a mammary gland disease or the possibility of onset of a mammary gland disease is high" when the measured CyPA level is higher than the reference value, whereas it is determined that "there is no onset of a mammary gland disease or the possibility of onset of a mammary gland disease is low" when the measured CyPA level is lower than the reference value. As another embodiment of qualitative determination, it is determined that "there is the onset of a mammary gland disease or the possibility of onset of a mammary gland disease is high" when a rise of the measured CyPA level is observed and "positive" rating is given, whereas it is determined that "there is no onset of a mammary gland disease or the possibility of onset of a mammary gland disease is low" when no rise of measured CyPA level is observed and "negative" rating is given.

As an example of quantitative determination, the possibilities (%) of onset of a mammary gland disease are assigned in advance to respective measured CyPA ranges as shown below and the possibility of onset of a mammary gland disease (%) of an udder or udder quarter of a subject is determined from the measured CyPA level: the possibility of onset of a mammary gland disease is determined to be not higher than 10% when the measured CyPA level is within the range between a and b; the possibility of onset of a mammary gland disease is determined to be between 10% and 30% when the measured CyPA level is within the range between b and c; the possibility of onset of a mammary gland disease is determined to be between 30% and 50% when the measured CyPA level is within the range between c and d; the possibility of onset of a mammary gland disease is determined to be between 50% and 70% when the measured CyPA level is within the range between d and e; the possibility of onset of a mammary gland disease is determined to be between 70% and 90% when the measured CyPA level is within the range between e and f; the onset of a mammary gland disease is determined when the measured CyPA level is higher than f.

When determining the onset of a mammary gland disease or the possibility of onset of a mammary gland disease, other indicators for determining a mammary gland disease (PL test, CL activity etc.) can be utilized in addition to CyPA. For example, when determining the onset of a mammary gland disease or the possibility of onset of a mammary gland disease by means of the CyPA level and the CL activity, firstly the onset of a mammary gland disease or the possibility of onset of a mammary gland disease is determined based on the measured CyPA level and, if it is determined that the possibility of onset of a mammary gland disease is high, an operation of detecting the CL activity is additionally conducted and then the possibility of onset of a mammary gland disease is determined by comprehensively judging the detected results of the measured CyPA level and the detected CL activity. In other words, the measured CyPA level is utilized for the primary determination and the result of detection of the CL activity is utilized for the secondary determination or the final determination. Conversely, the result of detection of the CL activity or some other indicators for determining a mammary gland disease may be utilized for the primary determination.

In a preferable mode Step (2) employed in the method of the present invention, it is determined that there is the onset of a mammary gland disease or there is a possibility of onset of a mammary gland disease in the sample udder or the sample udder quarter when the measured CyPA level is higher than the CyPA level in the milk collected from a healthy udder or udder quarter, which is called a reference CyPA level.

With the method of the present invention, a healthy udder or udder quarter is preferably an udder or udder quarter that has not shown any onset of the mammary gland disease or any possibility of onset of the mammary gland disease in the past from the viewpoint of avoiding any false determination, although an udder or udder quarter that does not show any onset of the mammary gland disease or any possibility of onset of the mammary gland disease just at present is acceptable as a healthy udder or udder quarter. As for an udder or udder quarter that has shown the onset of a mammary gland disease or the possibility of onset of a mammary gland disease in the past, the udder or udder quarter can be used as healthy udder or udder quarter so long as it does not show any onset of the mammary gland disease or any possibility of onset of the mammary gland disease at present because it has been appropriately treated. However it is desirable that such a determination may be made very deliberately.

No particular limitations are provided for collecting milk from a healthy udder or udder quarter in terms of method and timing of milk collection. For example, the operation of collecting milk from a healthy udder or udder quarter can be executed by using the same method as the one that is used for collecting milk from an udder or an udder quarter of a subject at the time of collecting milk from the udder or udder quarter of the subject simultaneously or at some other time. Additionally, no particular limitations are provided for detecting the CyPA level in the milk collected from the healthy udder or udder quarter in terms of detection method and timing. For example, the operation of detecting the CyPA level can be executed for a healthy udder or udder quarter by using the identical method as the method for detecting the CyPA level in the milk collected from an udder or an udder quarter of a subject simultaneously at the time of executing the operation of detecting the CyPA in the milk collected from the udder or udder quarter of the subject or at some other time.

In examples that are described hereinafter, the milk of Analysis No. 42 is used as milk collected from a healthy udder or udder quarter. With the method of the present invention, like the milk of Analysis No.42, each of the milk samples collected from the respective udder quarters of a subject (udder quarter milk samples) may be determined as "milk collected from a healthy udder or udder quarter" when it satisfies the requirements (1) that the PL test result is negative, (2) that the CL activity is less than $1 \times 10^6$ cpm/mL, and (3) that the milk quality is free from abnormalities (flakes and clots, a high viscosity). In other words, in examples as described hereinafter, each of the milk samples of Analysis Nos. 41 through 44 can be adopted as "milk collected from a healthy udder or udder quarter".

Figure 11:
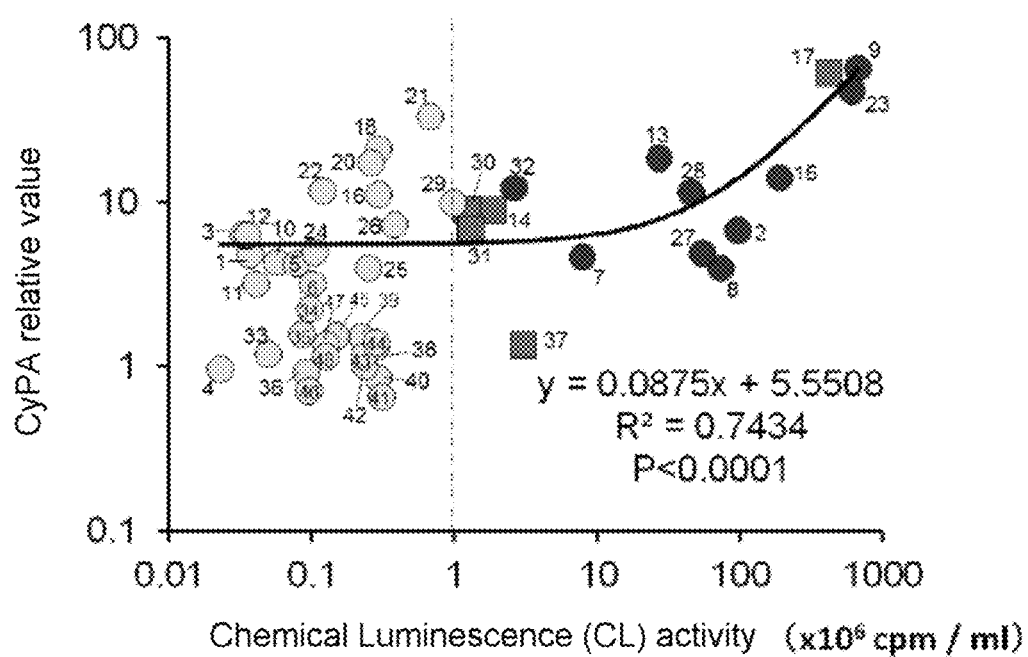
FIG. 11 is a graph showing the correlation of the chemical luminescence activity and the CyPA expression level in milk. More specifically.

FIG. 11 shows a fact proving that the measured CyPA levels of the milk samples (Analysis Nos. 2, 7, 8, 9, 13, 15, 23, 27, 28, 32) for which the PL test conducted were positive on them were higher than the reference CyPA level determined from the milk samples (Analysis Nos. 41 through 44) collected from a healthy udder or udder quarter. In view of this fact, in a preferable mode of Step (2) employed in the method of the present invention, if the measured CyPA level is higher than the reference CyPA level or not can be applied as criterion for determination. More specifically, it is determined that a mammary gland disease has been developed or possibly developed in the udder or udder quarter of the subject when the measured CyPA level is higher than the reference CyPA level.

The lowest value of the measured CyPA levels in the milk samples that were positive in the PL test in FIG. 11 (4.043; Analysis No. 8) was 2.8 times of the highest value of the reference CyPA values (1,419; Analysis No. 44) and 3.8 times of the average value of the reference CyPA values (1.065). Thus, on the basis of these results, in a preferable mode of Step (2) employed in the method of the present invention, it is determined that a mammary gland disease has been developed or possibly developed a mammary gland disease in an udder or udder quarter of a subject preferably when the measured CyPA level is not lower than twice of the reference CyPA level, more preferably when the measured CyPA level is not lower than 2.8 times of the reference CyPA level, further preferably when the measured CyPA level is not lower than 3.3 times of the reference CyPA level and particularly preferably when the measured CyPA level is not lower than 3.8 times of the reference CyPA level.

In another mode of carrying out the method of the present invention, there is provided a method of examining a mammary gland disease comprising steps (1') and (2') listed below;
(1') a step of detecting CyPA in a mammary gland collected from an udder or an udder quarter of a subject, thereby determining the CyPA level in the mammary gland; and)
(2° a step of determining the onset of a mammary gland disease or the possibility of onset of a mammary gland disease in the udder or the udder quarter of the subject on the basis of the CyPA level in the mammary gland.

Step (1') employed in the second method of the present invention can be executed by applying Step (1) employed in the first method. There are no particular limitations to the technique of collecting a mammary gland from an udder or an udder quarter of a subject. For example, any techniques those who are skilled in the art normally employ for collecting a mammary gland such as a paracentesis and suction technique of inserting a syringe needle into the udder and sucking mammary epithelial cells to collect part of the mammary gland there, and a technique of cutting part of the mammary gland tissue and collecting the cut part can be used for Step (1'). There are no particular limitations to the techniques of detecting CyPA in a mammary gland and any means of detecting a particular protein, polypeptide or mRNA from cells and tissues may be used for the purpose of the present invention.

The exemplary procedure described below can be used for Step (1') employed in the second method of the present invention. Firstly, a syringe needle is inserted into an under quarter of a subject to suck mammary epithelial cells. Then, the mammary epithelial cells obtained by the suction are provided with labelled anti-CyPA antibody. Thereafter, the absolute CyPA level or the CyPA level per cell is detected by means of observation through a fluorescence microscope or by flow cytometry, using the labelling substance of the labelled anti-CyPA antibody as indicator.

As for another exemplar procedure that can be used for Step (1') employed in the second method of the present invention, the CyPA level may be detected for the collected mammary gland tissue by means of an immunohistochemical technique or a technique similar to the technique of detecting the CyPA level in milk from the homogenate such as mammary epithelial cells collected. There are no particular limitations to collecting mammary gland and detecting the CyPA level so long as the CyPA level to be detected can be compared with a corresponding reference value.

Step (2') employed in the second method of the present invention can be executed by applying Step (2) employed in the first method. In a preferable mode of executing Step (2') employed in the second method of the present invention, it is determined that an udder or an udder quarter of a subject has the onset of a mammary gland disease or a possibility of onset of a mammary gland disease when the CyPA level in the mammary gland is higher than the CyPA level in the mammary gland tissue collected from a healthy udder or udder quarter.

With the method of the present invention, a step other than the above described steps may also be adopted if it is possible to eventually determine the onset of a mammary gland disease or the possibility of onset of a mammary gland disease of an udder or an udder quarter of a subject by adopting such a step. More specifically, another step may be arranged between Step (1) and Step (2) or between Step (1') and Step (2'). In other words, the method can be modified and altered in various different ways so long as such modifications and alterations are within the imaginable and conceivable scope to those who are skilled in the art on the basis of the state of the art.

The method of the present invention can be utilized for various purposes. More specifically, the method can be utilized, for example, as method of confirming the prognosis of a mammary gland disease, as method of confirming the progress of treatment of a mammary gland disease, as method of confirming the appropriateness of treatment of a mammary gland disease, as method of confirming the effect of treatment of a mammary gland disease and as method of screening treatment agents for a mammary gland disease.

As a specific example, it is conceivable to provide a method comprising a step of determining the CyPA level in milk or in a mammary gland by detecting CyPA in the milk collected from an udder or an udder quarter of a subject to whom a mammary gland disease treatment agent has been administered and a step of confirming or determining the progress, the appropriateness or the effect of the treatment of the mammary gland disease in the udder or the udder quarter of the subject on the basis of the CyPA level in the milk or mammary gland including the CyPA level in the milk or mammary gland collected from a healthy udder or udder quarter or the CyPA level in the milk or mammary gland that has been observed in the course of time, days, weeks, months or years. As another example, it is also conceivable to provide a method comprising a step of determining the CyPA level in milk or in a mammary gland by detecting CyPA in the milk collected from an udder or an udder quarter of a subject to whom a test substance such as a compound, a protein and an antibody has been administered, a step of evaluating the treatment effect and/or the preventive effect for a mammary gland disease on the basis of the CyPA level in the milk or the mammary gland, and a step of determining as mammary gland disease treatment agent the test substance that is evaluated to show a high treatment effect and/or a high preventive effect.

2. Reagent for Examining a Mammary Gland Diseases

A reagent for examining a mammary gland disease according to the present invention comprises an anti-cyclophilin A antibody (anti-CyPA antibody). There are no particular limitations to an anti-CyPA antibody according to the present invention in terms of type and origin so long as it has specific affinity for CyPA. An anti-CyPA antibody according to the present invention may be either a monoclonal antibody or a polyclonal antibody. Examples of polyclonal antibody include an IgG fractions originating from antiserum collected from an immune animal and antibodies obtained by affinity purification from antiserum using CyPA as antigen. Furthermore, commercially available antibodies such as abcam (registered trademark) rabbit-anti-human CyPA (polyclonal antibody) can also be used. The above commercially available antibodies are those that recognize human CyPA antibodies but can also specifically be bound to CyPA in cow milk. In this way, anti-CyPA antibodies whose antigen recognizing sites are derived from hetero types can be used so long as they can specifically be bound to CyPA in the subject.

There are no particular limitations to anti-CyPA antibody in terms of structure so long as it has specific affinity for CyPA. Similarly, there are no particular limitations to the globulin types of anti-CyPA antibody. For example, it may be IgG, IgM, IgA, IgE, IgD or the like. Also, it may be a fragmented antibody like Fab, Fab', F(ab')$_2$, scFv or dsFv antibody.

Anti-CyPA antibody can be prepared by utilizing one of methods such as immunological methods, phage display methods and liposome display methods. Monoclonal antibody and polyclonal antibody can be prepared by means of an immunological method and by referring without limitations to the following description.

When preparing monoclonal antibody, firstly antigen of CyPA or partial peptide thereof is administered by itself or with a carrier and a diluent to a site of a mammal that is capable of producing antibody. At the time of administration, a perfect Freund's adjuvant or an imperfect Freund's adjuvant may also be administered in order to improve the antibody production by the administration.

While there are no particular limitations to the method of obtaining antigen, it can be obtained from a biological specimen such as mammary epithelial cells by means of isolation and purification or as recombinant prepared by means of a genetic engineering technique on the basis of information on the amino acid sequence described at sequence ID No. 1 in the sequence listing. For example, the recombinant can be prepared by introducing a gene encoding an antigen or part thereof into an appropriate vector, then introducing a recombinant vector into an appropriate host and giving rise to express CyPA or part thereof in the obtained transformant.

Antigen is administered to a mammal normally once in every two to six weeks to a total of about two to ten times. Mammals that can be used for this purpose include monkeys, rabbits, dogs, guinea pigs, mice, rats, sheep and goats, of which mice and rats are preferably employed.

Then, an individual whose antibody titer is recognized is selected from the mammals that are immunized by the antigen. Thereafter, the spleen or lymph nodes are collected two to five days after the last immunization to obtain antibody-producing cells. Spleen cells are preferable as antibody-producing cells. Monoclonal antibody-producing hybridoma can be prepared by fusing the obtained antibody-producing cells, for example, with myeloma cells of an animal of the same species or of the different species. Such a fusion operation can be executed according to a known method such as the Keller and Milstein method (Nature, 256, 495 (1975)). There are no particular limitations to the fusion accelerator to be used for the fusion operation. Examples of fusion accelerators include polyethylene glycol (PEG) and Sendai virus, of which PEG is preferably employed.

While there are no particular limitations to myeloma cells to be used for this purpose, examples of myeloma cells that can be used for this purpose include myeloma cells of mammals such as NS-1, P3U1, SP2/0 and AP-1, of which SP2/0 is preferably employed. Cell fusion can be effectively executed on condition that sets the ratio of the number of antibody producing cells (preferably spleen cells) to the number of myeloma cells at preferably about 1:1 through about 20:1, adds PEG (preferably PEG1000~PEG6000, more preferably PEG4000) with a concentration of about 10 to about 80%, and incubates the cells at 20 to 40° C., preferably at 30 to 37° C., for 2 minutes.

Cultivation of hybridoma can be realized by using a culture medium for animal cells to which HAT (hypoxantin, aminopterin, thymidine) is added. For example, RPM-1640 medium containing bovine embryo serum by 1 to 20%, preferably 10 to 20%, GIT medium containing bovine embryo serum by 1 to 10% (available from Wako Pure Chemical Industries) or non-serum medium for culturing hybridoma (SFM-101: trade name, available from Nissui Pharmacetical) can be employed. The cultivation temperature is normally 20 to 40° C., preferably about 37° C. The cultivation time is normally between 4 days and 2 weeks, preferably about 1 week. The cultivation is normally conducted in the presence of 5% carbon dioxide gas.

After hybridoma is turned into monoclonal, clone that produces anti-CyPA antibody, which is highly specific against CyPA, is selected. The target monoclonal anti-CyPA antibody is obtained by purifying the culture broth of the selected clone. Alternatively, the target monoclonal anti-CyPA antibody can be obtained by growing hybridoma beyond a predetermined number, subsequently transplanting them into the abdominal cavity of a mammal (such as mouse), further growing the hybridoma in the ascites of the mammal and then purifying the ascites.

Affinity chromatography that uses an affinity chromatography column for purifying monoclonal IgM, affinity chromatography that uses protein G, protein A or the like is employed to purify the culture broth or the ascites. Alternatively, affinity chromatography by which CyPA, which is antigen, is immobilized can be employed. Furthermore, the monoclonal antibody can be isolated and purified by employing a method that is known per se and selected from a group of techniques for isolating and purifying immune globulin that are known to those who are skilled in the art, which includes salt precipitation, ammonium sulfate fractionation, alcohol precipitation, isoelectric point precipitation, electrophoresis, adsorption-desorption by ion exchanger such as DEAE, ultra-centrifugation, gel filtration, antigen binding solid phase and specific purification of collecting only antibody by means of active adsorption agent such as protein A or protein G thereby dissociating the binding to obtain antibody. One of these techniques may be used alone or in combination with one or more other techniques.

Polyclonal antibody against the antigen of CyPA or partial peptide thereof can be manufactured by any of the existing methods that are known per se. For example, polyclonal antibody against the antigen of CyPA can be obtained by preparing the antigen to be immunized or a complex of the antigen and a carrier protein, then immunizing a mammal by a method similar to the above described method of preparing monoclonal antibody, thereafter collecting the substance containing anti-CyPA antibody from the obtained immunized animal at the time when the antibody titer rises appropriately and then isolating and purifying the antibody.

A complex of the immunized antigen and a carrier protein may be used as antigen. Examples of carrier proteins that can be used for the purpose of the present invention include KLH (keyhole limpet hemocyanin), BSA (bovine serum albumin) and OVA (ovalbumin). Techniques that can be used to bind the carrier protein include the carbodiimide method, the glutaraldehyde method, the diazo condensation method and the maleimide benzoyl oxisuccinimide method. Furthermore, antigen whose structure is partly modified such as a protein that is fused with a histidine (His) tag or the like can also be employed. Modified antigen such as fused protein can be prepared and purified by means of a general purpose method that is known to those who are skilled in the art.

While there are no particular limitations to the type of carrier protein and the mixing ratio of the carrier and hapten so long as the antibody can be prepared efficiently relative to the hapten that is cross-linked to the carrier and immunized. For example, a technique of coupling bovine serum albumin, bovine thyroglobulin, hemocyanine or the like to hapten to a ratio between about 0.1 and 20, preferably between about 1 and 5 relative to 1 on the part of hapten by weight can be employed.

Any of various condensation agents, e.g., activated ester reagents containing a dithiopyridyl group and a thiol group, glutal aldehyde, carbodiimide, maleimide active ester, is employed to couple hapten and the carrier.

Polyclonal antibody can be collected from blood, ascites or the like, preferably from blood, of a mammal immunized by the above described method. The polyclonal antibody titer in the antiserum obtained by centrifugation of the blood collected from an immunized animal can be measured by, for example, causing labelled CyPA that is labelled by a labelling agent such as enzyme and fluorescence to react with the antiserum and subsequently measuring the quantity and the level of activity of the labelling agent bound to the antibody. Polyclonal antibody can be isolated and purified by means of methods for isolation and purification of immune globulin similar to the isolation and purification of the above described monoclonal antibody. For example, the antiserum can be turned to polyclonal antibody by affinity purification of the antiserum.

Furthermore, anti-CyPA antibody can be prepared by means of a genetic engineering technique or a molecular biological technique. For example, anti-CyPA antibody can be prepared by analyzing the antigen recognizing site in the antibody that recognizes CyPA originating from a subject, which may be a bovine or the like, and obtaining the nucleic acid encoding the recombinant antibody, that has the antigen recognizing site and the other parts of which is derived from the subject. Besides, antibody that is turned into a complete antibody for a subject, which may be a bovine, can be obtained by introducing the gene that is involved in producing antibody of the subject into an embryo of an animal of some other species, which may for example be a mouse, or into an antibody producing cell originating from a mouse and using the obtained mouse and mouse antibody producing cell and CyPA originating from the bovine as antigen. Known genetic engineering techniques and known molecular biology techniques can be used for those methods without limitations. For examples, the techniques described in Molecular Cloning: A Laboratory Manual, 2nd Ed., Cold Spring Harbor Laboratory, Cold Spring Harbor, N.Y., 1989 and Current Protocols in Molecular Biology Supplement 1-38, John Wiley & Sons (1989-1997) etc. can be referred to, (the contents of which are incorporated herein by reference for the purpose of supporting the disclosure of the present invention).

Anti-CyPA antibody may be modified in various different ways on condition of keeping specific affinity for CyPA. Such modified antibody can also be used as reagent for the purpose of the present invention.

When labelled antibody is used as anti-CyPA antibody, the bound quantity of antibody can directly be detected by using a labelling agent as indicator. Therefore, labelled anti-CyPA antibody is an embodiment of anti-CyPA antibody.

There are particular limitations to the labelling agent to be used for the purpose of the present invention. Examples of labelling agents include enzymes such as peroxidase, microperoxidase, horse radish peroxidase (HRP), alkaline phosphatase, β-D-galactosidase, glucose oxidase and glucose-6-phosphalic acid dehydrogenated enzyme; fluorescent substances such as fluorescein isothiocyanate (FITC), tetramethyl rhodamine isothiocyanate (TRITC), europium, phycoerythrin (PE), Cy2, Cy3 and Cy5; chemiluminescent substances such as luminol, isoluminol and acridinium derivatives; coenzymes such as NAD; specific proteins such as biotin; and radioactive substances such as 131I and 125I.

For example, if peroxidase is employed as labelling agent, DAB (3,3'-diaminobenzidinetetra hydrochloride), OPD (o-phenylenediamine hydrochloride) and the like can be utilized as chromogenic substrate. As other examples, bromochoro indole phosphate/nitro blue tetrazolium and NPP (p-nitrophenyl phosphate disodiumsalt hexahydrate) and the like can also be utilized as chromogenic substrate when alkaline phosphatase is employed as labelling agent.

The reagent of the present invention may be immobilized onto an insoluble carrier depending on the application. While there are no particular limitations to the insoluble carrier to be used for such immobilization, examples of insoluble carriers include resins such as polystyrene resin, polycarbonate resin, silicon resin, nylon resin and fluorine resin, glass-based materials such as beads, plates and thin film; porous materials such as unwoven clothes and paper filters; and other carriers that are insoluble to water. There are no particular limitations to the method of immobilizing antibody to an insoluble carrier. Techniques based on physical adsorption or chemical adsorption, which are normally known to those who are skilled in the art, can be used for this purpose.

3. Kit for Examining a Mammary Gland Disease

A kit according to the present invention comprises a reagent according to the present invention as principal component. A kit according to the present invention may further comprise one or more tools and devices (container, reaction device, florescence reader, etc.) in addition to other one or more reagents (buffer solution, blocking reagent, enzyme substrate, luminescence reagent, etc.) to be used when the method of examining a mammary gland disease is put to execute. Furthermore, a kit according to present invention preferably comprises CyPA as standard reagent. Moreover, a kit according to the present invention may further include reagents, tools, devices and so on to be used for methods of examining a mammary gland disease executed for the other purpose than detection of CyPA. For example, a kit according to the present invention may comprise a reagent, a tool and/or a device for PL tests for the purpose of improving determination accuracy of mammary gland disease. Like commercially available similar kits, an operation manual is preferably attached to a kit according to the present invention.

In a kit according to the present invention, the anti-CyPA antibody may be labelled. When the anti-CyPA antibody that is the primary antibody to be bound to antigen is labelled, there arises a problem that the antigen detection sensitivity of the kit is reduced. Therefore, an indirect detection method such as a method of utilizing secondary antibody to which a labelling agent is bound or a method of utilizing a carrier to which secondary antibody and a labelling agent are bound may be preferably employed. While there are no particular limitations to the secondary antibody so long as it shows specific affinity for anti-CyPA antibody. For example, antirabit IgG antibody may be used when anti-CyPA antibody is prepared as rabit antibody. Labelled secondary antibodies that can be used for antibodies of various species including rabbits, goats and mice are commercially available from, for example, Takara Bio and Cosmo Bio). Therefore, an appropriate labelled secondary antibody may be selected according to the reagent of the present invention and a kit according to the present invention may be made to comprise the selected labelled secondary antibody.

In a preferable mode, a kit according to the present invention comprises anti-CyPA antibody (primary antibody) which is a reagent according to the present invention and labelled antibody (secondary antibody) against the anti-CyPA antibody. When anti-CyPA antibody that is a reagent according to the present invention is immobilized, the secondary antibody preferably has an antigen recognizing site for recognizing epitope that differs from the epitope the primary antibody recognizes. In a preferable mode, a kit according to the present invention were preferably comprises a reagent for detecting immune complexes including chromogenic substrates and chromogenic reagents, depending on the type of labelling reagent. In another preferable mode, a kit according to the present invention comprises a porous carrier that includes site A where a sample is to be applied, site B that contains labelled antibody and site C, which is an antigen detecting site. The site B that contains labelled antibody is made to contain labelled antibody against CyPA that is movable in a wet state. At the antigen detecting site C, anti-CyPA antibody against CyPA for recognizing a site different from the site that labelled antibody recognizes is immobilized. Anti-CyPA antibody forms a sandwich-like complex (labelled antibody-CyPA-anti-CyPA antibody) by way of labelled antibody to which CyPA is bound and CyPA. The site A where a sample is to be applied and site B that contains labelled antibody may be located at a same position. In this mode, when CyPA exists in a liquid sample and the liquid sample is applied to the site A where sample is to be applied, CyPA and labelled antibody are bound to each other at site B that contains labelled antibody and, if the bound product moves to the site C that is an antigen detecting site, the bound product is captured by forming a complex with the immobilized anti-CyPA antibody. When, therefore, a labelling substance such as colored latex, dye sol, gold colloid or the like that can be made visible to naked eyes is employed, the presence and/or the quantity of CyPA in the sample can be confirmed by detecting the existence or non-existence of the label at the site C that is an antigen detecting site.

4. Anti-CyPA Antibody Producing Hybridoma and Anti-CyPA Antibody

A hybridoma according to the present invention has an ability of producing anti-CyPA antibody. An antibody according to the present invention is anti-CyPA antibody that is produced by a hybridoma according to the present invention. There are no particular limitations to a hybridoma according to the present invention so long as it is a fused cell obtained by fusing an antibody producing cell having an ability of producing anti-CyPA antibody and a tumor cell such as myeloma cell or an immortalized cell. There are no particular limitations to an antibody according to the present invention so long as it has specific affinity for CyPA. With regard to the structure and function of a hybridoma and/or an antibody according to the present invention as well as the techniques of confirming, producing and using a hybridoma and/or an antibody according to the present invention, the above-mentioned descriptions on anti-CyPA antibodies and hybridomas that produce anti-CyPA antibody can be referred to.

Beside the above described method of obtaining a hybridoma and an antibody according to the present invention, as described in Examples hereinafter, a hybridoma and an antibody according to the present invention can also be obtained by screening monocronal antibodies that are specific to M-BIE cells originating from bovine intestinal epithelial cell line (BIE cells). More specifically, a mammal (e.g. mouse) is immunized by M-BIE cells and antibody producing cells are extracted from the immunized mammal. Then, the antibody producing cells and the myeloma cells of a mammal (mouse) of a species same as the immunized mammal are subjected to cell fusion to obtain hybridoma by means of cultivation using an HAT medium. Thereafter, hybridoma that produces antibody capable of specifically recognizing FAE at bovine intestinal epithelium is selected by means of immunohistochemical staining and cloned. Subsequently, the cloned cells are intraperitoneally administered to a mouse and the monocronal antibody (2H5-F3) originating from mouse ascites is isolated and purified. Then, 2H5-F3 monoclonal antibody and the protein collected from the cytoplasm fraction and the cell membrane fraction of M-BIE cells are mixed and subjected to immune-precipitation. Then, the protein solution obtained by the immune-precipitation is isolated by SDS-PAGE and the bands are stained. Thereafter, the bands that are specific to 2H5-F3 monoclonal antibody is analyzed to find out that the antigen that 2H5-F3 monoclonal antibody specifically recognizes is CyPA. Thus, the 2H5-F3 monoclonal antibody is identified as anti-CyPA antibody.

5. Marker for Detecting a Mammary Gland Disease

A marker according to the present invention is a marker for detecting a mammary gland disease comprising cyclophilin A. A marker according to the present invention refers to a biological molecule that can serve as indicator of onset or of possibility of onset of a mammary gland disease, in particular mastitis which is an infectious mammary gland disease. A marker according to the present invention is not cyclophilin A itself existing in a living body but cyclophilin A isolated from the mammary gland or the milk collected from a living body is utilized as a marker according to the present invention. A marker according to the present invention is particularly useful for early detection of mastitis.

That a marker according to the present invention is useful for early detection of mastitis can be reasoned from the fact found first by the inventors of the present invention that, as a result of careful observations of the onsets and phenomenal aspects of mastitis, an increase in the CyPA expression level was recognized in cow mammary epithelial cells and at sites of infiltrated immune cells of mammary gland tissues where the onset of mastitis is found and even in milk collected from mastitis-infected mammary glands if compared with normal mammary gland tissues. Particularly, the inventors of the present invention confirmed the fact that the CyPA concentration is relatively high in udder quarters that have been determined for the onset of mastitis by means of the PL test and the CL activity which are a known mastitis examination method. In view of this fact, therefore, a marker according to the present invention is a marker to be used for determining the onset of latent mastitis in addition to determining the onset of clinical mastitis.

Additionally, the inventors of the present invention found milk samples where no structural changes in the milk proteins were observed but an increase of CyPA level was confirmed, although the milk samples were negative for the PL test and had the low level of CL activity. Furthermore, the inventors of the present invention found the fact that the onset of mastitis was recognized in some of the udder quarters from which these milk samples were collected. According to these findings, a marker according to the present invention is a marker that can highly sensitively detect a possible onset of mastitis that can hardly be determined by means of a PL test or CL activity in addition to the capability of early mastitis detection of the marker, when CyPA is used as indicator. In other words, it is possible to identify the site where mastitis is in early stages by means of a marker according to the present invention.

Hereinafter, the present invention will be explained in greater detail with the use of examples, although the examples never limit the scope of the present invention by any means.

EXAMPLES

1st Localization of Cyclophilin A in Mammary Gland Tissue
1. Materials and Methods
(1) Samples The mammary gland tissues collected from the udders where the onset of experimental mastitis or latent mastitis was observable out of lactating Holstein cows of three different experimental districts indicated as A through C below were selected and used as mammary gland tissues developing mastitis. The mammary gland tissues were collected immediately after slaughtering the cows and were immobilized in a single night at 4° C. by quickly using PLP fixative solution or phosphoric acid buffer formalin fixative solution. After the fixation, the tissues were immersed sequentially in 70% ethanol, in 80% ethanol, in 90% ethanol and in 95% ethanol for 12 hours each and then in 100% ethanol for 24 hours so as to be dehydrated stepwise. After the dehydration, the tissues were immersed in each of toluene and paraffin for 6 hours and then embedded in paraffin. Additionally, the mammary gland tissues collected from mammary udders that were treated by administering PBS out of the lactating Holstein cows in each of the districts were used as control normal mammary gland tissues (see Toshinobu Kuroishi et al., Clin Diagn Lab Immunol. 2003:10:1011-1018 and Kai K et al. J Vet Med. Sci. 2002: 64:873-8, the contents of which are incorporated herein by reference for the purpose of supporting the disclosure of the present invention). The lactic acid bacteria producing peptide was purified according to the method described in Kawai et al.'s document (Kawai Y et al., Biosci Biotechnol Biochem. 1997:61:179-82, the contents of which are incorporated herein by reference for the purpose of supporting the disclosure of the present invention).

A. SEC Administration Experimental District

As the SEC administration experimental district, 0.1 µg/µl SEC solution, in which *Staphylococcal* Endotoxins C (SEC) was dissolved in PBS 10 mL, was administered into udder quarters of lactating Holstein cows byway of the related teats to cause the onset of mastitis to take place, and the udder quarters developing experimental mastitis (PLP-fixed paraffin-embedded mammary gland tissues; lactating Holstein cows; about 300 days after parturition) were obtained.

B. S. A. Administration Experimental District

As the S. A. Administration Experimental District, 154 cfu/ml S. A. solution, in which *Staphylococcus aureus* (S. A.) was dissolved in PBS 10 mL, was administered into udder quarters of lactating Holstein cows by way of the related teats to cause the onset of mastitis to take place, and the udder quarters developing experimental mastitis (phosphoric acid buffer formalin-fixed paraffin-embedded mammary gland tissues and mammary gland tissue obtained by biopsy; lactating Holstein cow; about 60 days after parturition) were obtained.

C. Lf Administration Experimental District

As the Lf administration experimental district, 10 mg/mL or 20 mg/mL lactoferrin (Lf) solution, in which Lf or lactic acid bacteria producing peptide was dissolved in PBS 10 mL, was administered into udder quarters of lactating Holstein cows byway of the related teats to cause the onset of mastitis to take place, and the udder quarters developing latent mastitis (PLP-fixed paraffin-embedded mammary gland tissue; lactating Holstein cows: about 305 days after parturition; non-lactating introduction 5 days) were obtained.

(2) Reagent

Localization of CyPA in mammary gland tissue was confirmed by immunohistochemical staining, using anti-CyPA antibody (2H5-F3 antibody) prepared by the inventors of the present invention. 2H5-F3 antibody was prepared by following the procedure that includes [i] and [ii] as described below.

[i] In Vitro Preparation of M Cell-Specific Monoclonal Antibody

The inventors of the present invention have established bovine intestinal epithelial cell line (BIE cells) and an in vitro method of differentiation induction thereof to M cells (M-BIE cells) (Characterization of newly established bovine intestinal epithelial cell line, K. Miyazawa, Histochem Cell Biol (2010) vol. 133, p 125-134, the contents of which are incorporated herein by reference for the purpose of supporting the disclosure of the present invention). M-BIE cells were adjusted to the concentration of $2.7 \times 10^6$ cells/ml-PBS and 0.5 ml of M-BIE cells were introduced and intraperitoneally injected to BALB/c mouse. Fourteen days thereafter, 0.3 ml of the M-BIE cells that had been adjusted to $4.0 \times 10^6$ cells/ml-PBS was administered into the same mouse by way of tail vein for additional immunization. Five days thereafter, spleen cells were collected from the immunized mouse and fused with SP2/0-ag14-K13 mouse myeloma cells by using 50% (w/v)polyethylene glycol (PEG4000). The fused hybridomas were selected by using a HAT medium (RPMI-1640 containing 2 mM glutamate, 0.2% glucose, 10% FBS, 100 µM hypoxanthine, 0.4 µM aminopterine and 16 µM thymidine). Then, wells that produce antibody capable of specifically recognizing FAE in bovine intestinal epithelium were selected from the selected hybridomas by immunohistochemical staining as described below and a further cloning operation was executed by limiting dilution. The cloned cells that were eventually obtained by the cloning were intraperitoneally administered to BALB/c mouse. The monoclonal antibody originating from ascites of BALE/c mouse was purified by means of HiTrap IgM Purification HP (GE Healthcare Bio-Science AB, Uppsala, Sweden). The subclass of the antibody was determined by means of a mouse monoclonal antibody isotyping kit (Dainippon Sumitomo Pharama) as 2H5-F3 monoclonal antibody.

[ii] Identification of Antigen that Prepared Antibody Recognizes

Cytoplasm fraction and cell membrane fraction of M-BIE cell and the proteins of each of them were collected by using Transmembrane Protein Extraction Kit (Novagen). 60 µl (2.0 µg/µl) of the proteins of the collected cell membrane fraction and 1.0 µl (2.45 µg/µl) of the 2H5-F3 monoclonal antibody were mixed with each other and left at rest overnight at 4° C. Then, the mixture was further mixed with 50 µl of µMACS protein G (Milteny Biotech) and left at rest for an hour at 4° C. and subsequently subjected to immunoprecipitation. The protein solution obtained as a result of the immunoprecipitation was isolated by SDS-PAGE and stained by means of Silver Stain MS kit (Wako). Bands that were specific to 2H5-F3 monoclonal antibody were extracted and subjected to LC-MS/MS analysis. Additionally, the protein obtained by immunoprecipitation was subjected to Western blotting and the reactivity with 2H5-F3 monoclonal antibody was analyzed. As a result, antigen that 2H5-F3 antibody recognizes was identified as cyclophilin A.

(3) Immunohistochemical Staining and Method of Confirming CyPA Localization

A 4-μm thick slice was prepared from paraffin-embedded mammary gland tissue of each of the experimental districts and immunohistochemically stained for CyPA by following the procedure shown below.

A. 1st Day

The mammary gland tissue obtained by deparaffinizing the slice was washed with water for 5 minutes and then subjected to an antigen activation process for 5 minutes at 121° C. by using Target Retrieval Solution Low pH (Dako). The processed mammary gland tissue was washed with PBS for 3 minutes 3 times. After the washing operation, the mammary gland tissue was subjected to a blocking process for 20 minutes by using 3% normal goat serum/PBS. The processed mammary gland tissue was subjected to a primary antibody reaction for 14 hours at 4° C. by using anti-CyPA antibody 2,000-times diluted/PBS.

B. 2nd day

After the reaction, the mammary gland tissue was washed with PBS for 3 minutes 3 times. After the washing operation, the mammary gland tissue was subjected to a secondary antibody reaction for 20 minutes at room temperatures by using Histofine Simplestain MAX-PO(M) (Nichirei). After the reaction, the mammary gland tissue was washed with PBS for 3 minutes 3 times. After the washing operation, the mammary gland tissue was subjected to a DAB chromogenic reaction for 1 minute at room temperature by using 0.0025% 3,3'-diaminobenzidine (Dojin, Kumamoto, Japan)+0.006% $H_2O_2$/0.05M Tris-HCl (pH 7.5). After the reaction, the mammary gland tissue was washed with distilled water (DW) for several seconds. After the washing operation, the mammary gland tissue was subjected to hematoxiline contrast staining for 20 seconds at room temperature. After the staining, the mammary gland tissue was washed with flowing water for 60 minutes. After the washing operation, the mammary gland tissue was dehydrated and cleared and subsequently mounted by using mounting medium Malinol (Muto Kagaku).

After the immunohistochemical staining, the mammary gland tissue sample was observed through an optical microscope (A×70, Olympus).

Figure 1B:
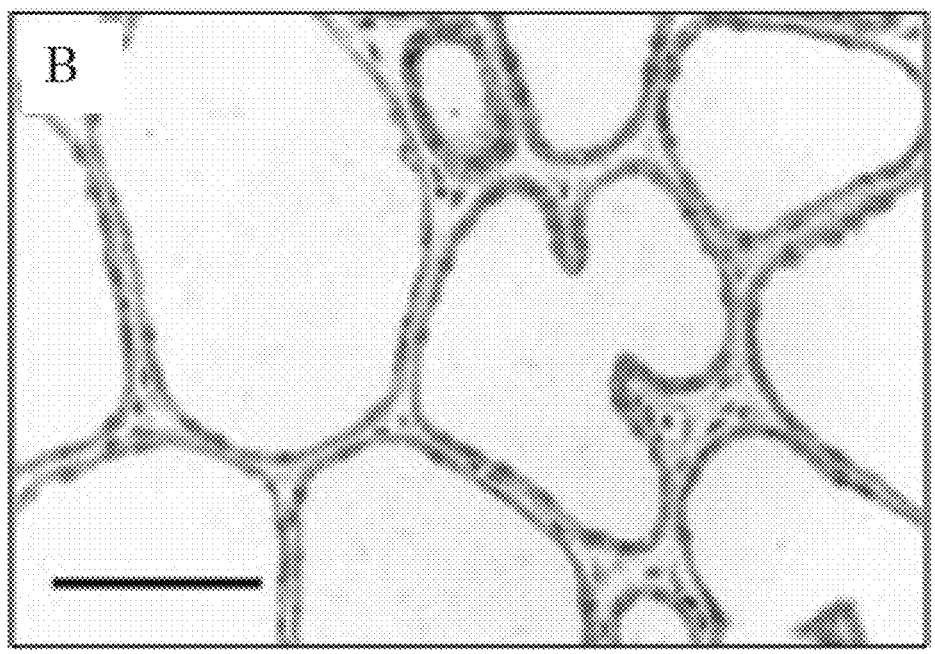
FIG. 1B is a picture illustrating localization of CyPA expression in a specimen of sliced mammary gland tissue in the mammary gland substratum prepared from a normal cow mammary gland of an SEC administration experimental mastitis district by immuno-staining with the use of anti-CyPA (2H5-F3 antibody). The figure proves that mammary alveoli are broad and mammary gland epithelial cells are flat, while CyPA expression is observed in all cells. The bar in FIG. 1B is 100 µm long.
Figure 1C:
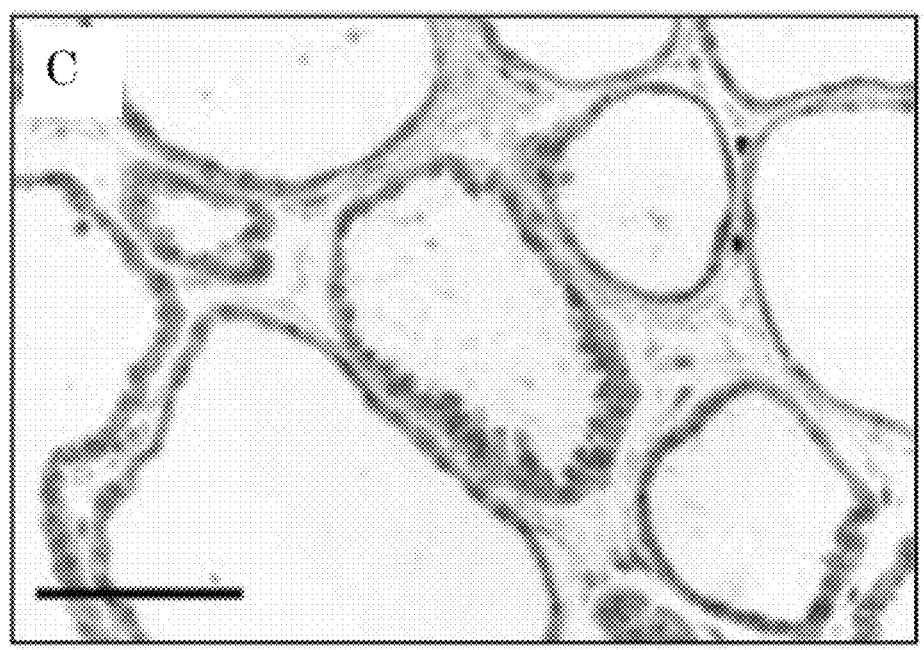
FIG. 1C is a picture illustrating localization of CyPA expression in a specimen of sliced mammary gland tissue in the mammary gland substratum prepared from a normal cow mammary gland of an SEC administration experimental mastitis district by immuno-staining with the use of anti-CyPA (2H5-F3 antibody). The figure proves that CyPA expression is weakly observed in cells synthesizing milk from mammary gland epithelial cells. The bar in FIG. 1C is 100 µm long.

2. Results (1) Observation of Mammary Gland Tissue by SEC Administration Experimental District CyPA expression in bovine mammary gland was observed by immunohistochemical staining. CyPA was localized in mammary alveoli in control normal mammary gland tissues of the SEC administration experimental district (FIG. 1A). There was uniform CyPA expression in mammary epithelial cells of mammary alveoli (FIG. 1B). Although weak, there was also CyPA expression in the milk found in mammary alveoli (FIG. 1C).

Figure 2A:
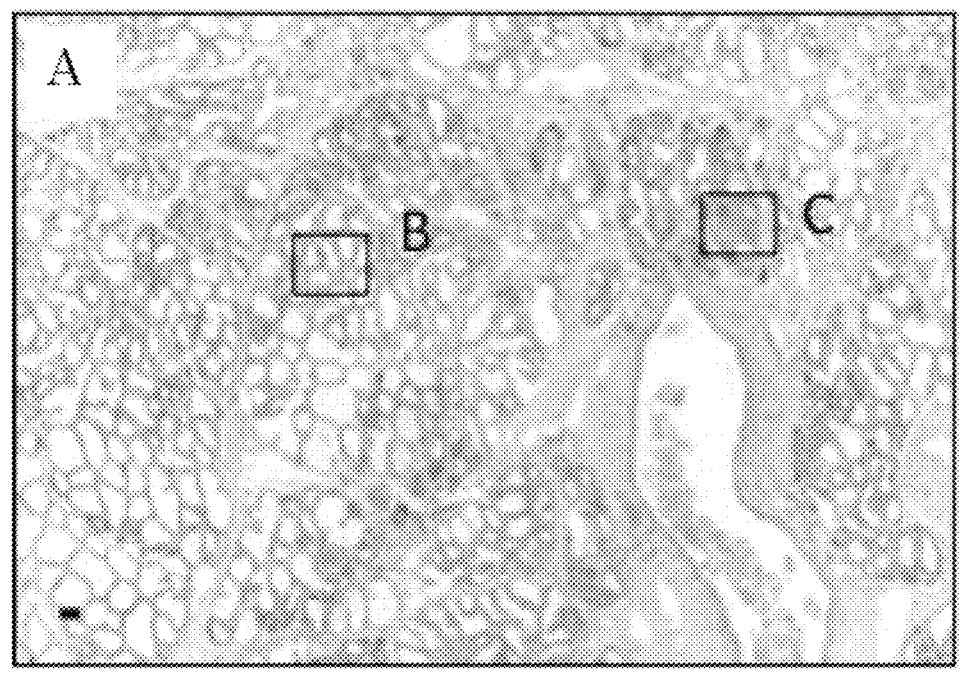
FIG. 2A is a picture illustrating localization of CyPA expression in a specimen of sliced mammary gland tissue in the mammary gland substratum prepared from a mastitis-infected cow mammary gland of an SEC administration experimental mastitis district by immuno-staining with the use of anti-CyPA (2H5-F3 antibody). The figure proves that, as inflammation occurs, interstitial hypertrophy arises and infiltration appears in many immune cells. The bar in FIG. 2A is 500 µm long.
Figure 2B:
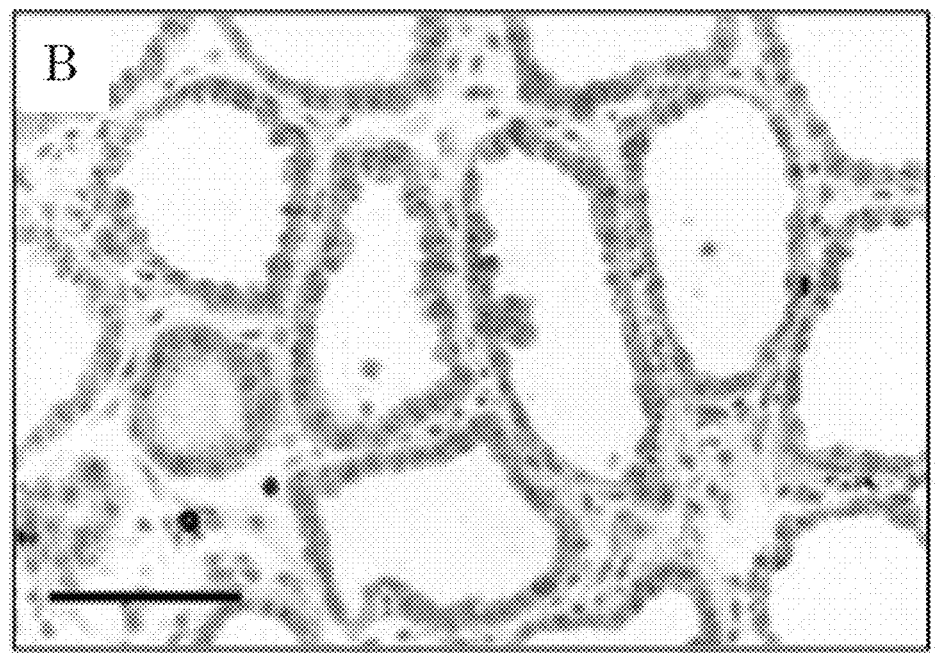
FIG. 2B is a picture illustrating localization of CyPA expression in a specimen of sliced mammary gland tissue in the mammary gland substratum prepared from a mastitis-infected cow mammary gland of an SEC administration experimental mastitis district by immuno-staining with the use of anti-CyPA (2H5-F3 antibody). The figure proves that, as atrophy of mammary alveoli occurs, mammary gland epithelial cells are deformed accordingly and the CyPA expression level becomes high. The bar in FIG. 2B is 100 µm long.
Figure 2C:
FIG. 2C is a picture illustrating localization of CyPA expression in a specimen of sliced mammary gland tissue in the mammary gland substratum prepared from a mastitis-infected cow mammary gland of an SEC administration experimental mastitis district by immuno-staining with the use of anti-CyPA (2H5-F3 antibody). The figure proves that CyPA expression is enhanced further at sites of strongly infiltrated immune cells and a large volume of CyPA is secreted into the milk in the mammary alveoli. The bar in FIG. 2C is 100 µm long.

The CyPA expression in the mammary gland tissue, where the onset of mastitis was observed, in the SEC administration experimental district was recognized in mammary epithelial cells as in control normal mammary gland tissues (FIG. 2A). However, when compared with control normal mammary gland tissues, CyPA expression was stronger in mammary gland epithelial cells, in milk and at cell infiltration sites of the mammary gland tissues where the onset of mastitis was observed (FIGS. 2B, 2C).

Figure 3A:
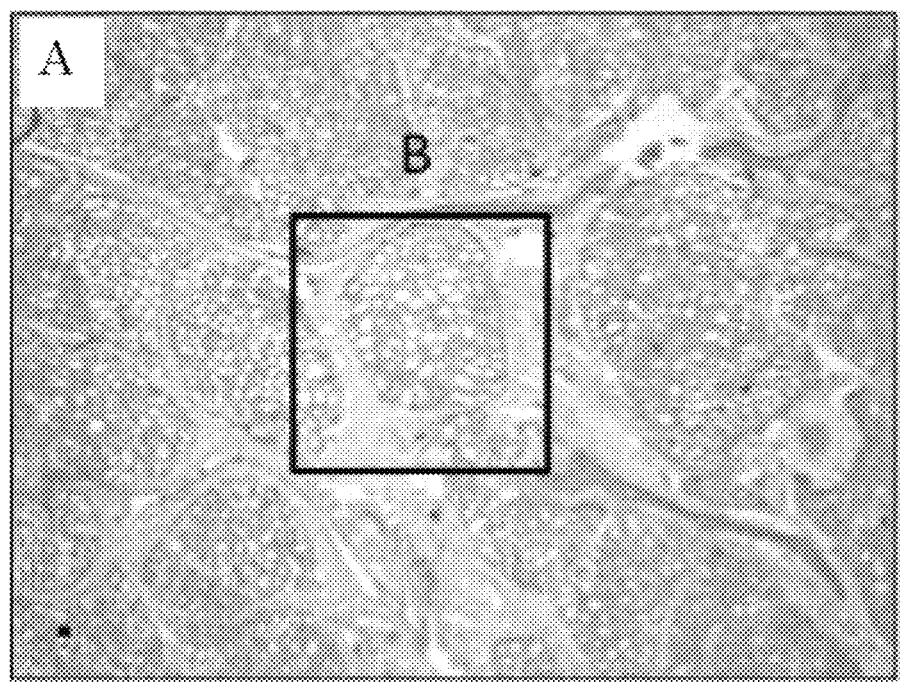
FIG. 3A is a picture illustrating localization of CyPA expression in a specimen of sliced mammary gland tissue in the mammary gland substratum prepared from a normal cow mammary gland of an S. A administration experimental mastitis district by immuno-staining with the use of anti-CyPA (2H5-F3 antibody). The figure proves that, while hypertrophy of supporting tissue is recognized, there is no site of infiltrated immune cell. The bar in FIG. 3A is 500 µm long.
Figure 3B:
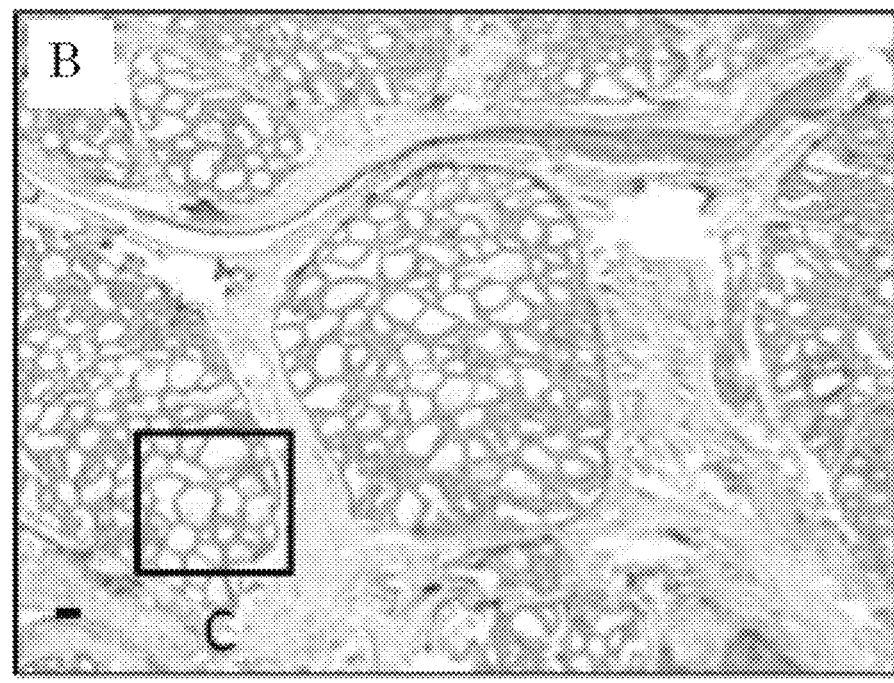
FIG. 3B is a picture illustrating localization of CyPA expression in a specimen of sliced mammary gland tissue in the mammary gland substratum prepared from a normal cow mammary gland of an S. A administration experimental mastitis district by immuno-staining with the use of anti-CyPA (2H5-F3 antibody). The figure proves mammary alveoli are broad and mammary gland epithelial cells are flat. The bar in FIG. 3B is 500 µm long.
Figure 3C:
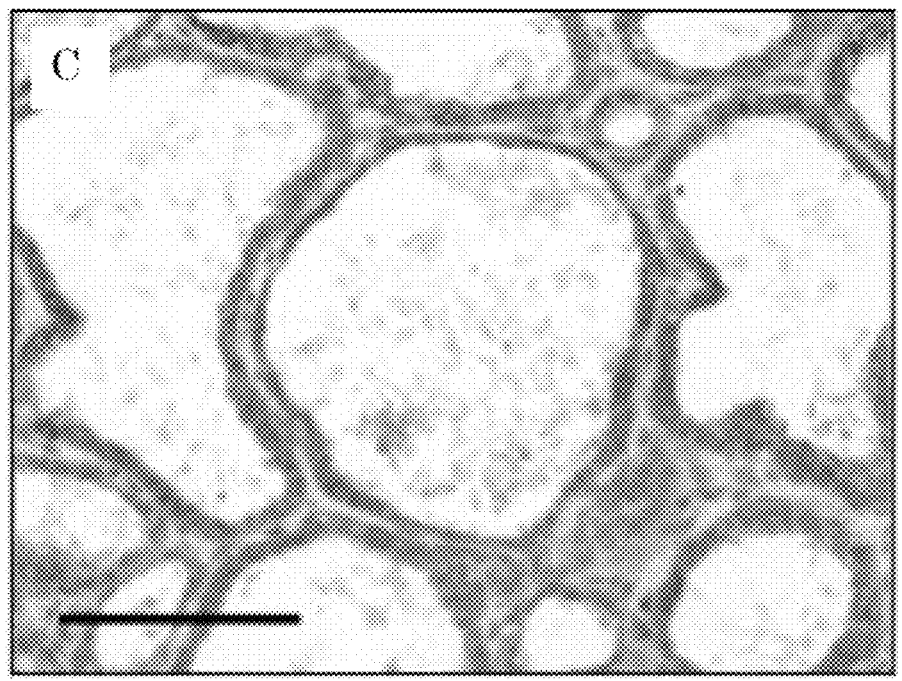
FIG. 3C is a picture illustrating localization of CyPA expression in a specimen of sliced mammary gland tissue in the mammary gland substratum prepared from a normal cow mammary gland of an S. A administration experimental mastitis district by immuno-staining with the use of anti-CyPA (2H5-F3 antibody). The figure proves that CyPA expression is observed in most mammary gland epithelial cells, while CyPA expression is slightly observed in secreted milk. The bar in FIG. 3C is 100 µm long.

(2) Observation of Mammary Gland Tissue by S. A. Administration Experimental District CyPA expression in cow mammary gland was observed by immunohistochemical staining. It was confirmed that, in control normal mammary gland tissues of the S. A. administration experimental district, there was uniform CyPA expression in mammary epithelial cells of mammary alveoli as in control normal mammary gland tissues of the SEC administration experimental district and that there was slight CyPA expression in the milk (FIGS. 3A through 3C).

Figure 4A:
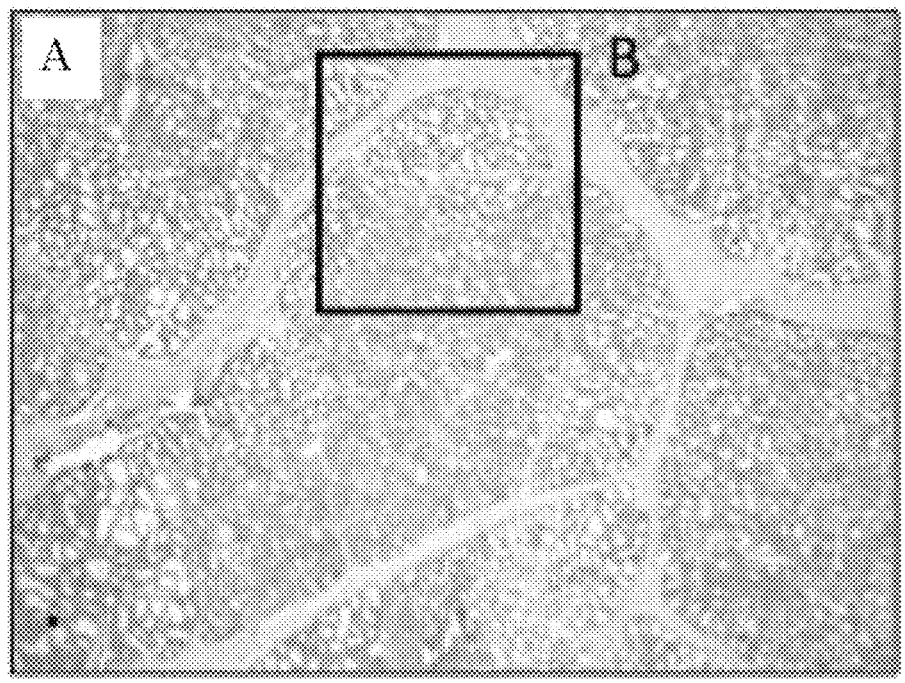
FIG. 4A is a picture illustrating localization of CyPA expression in a specimen of sliced mammary gland tissue in the mammary gland substratum prepared from a mastitis-infected cow mammary gland of an S. A administration experimental mastitis district by immuno-staining with the use of anti-CyPA (2H5-F3 antibody). The figure proves that in the inflammatory mammary gland, hypertrophy of supporting tissue and atrophy of some mammary alveoli occur. The bar in FIG. 4A is 500 µm long.
Figure 4B:
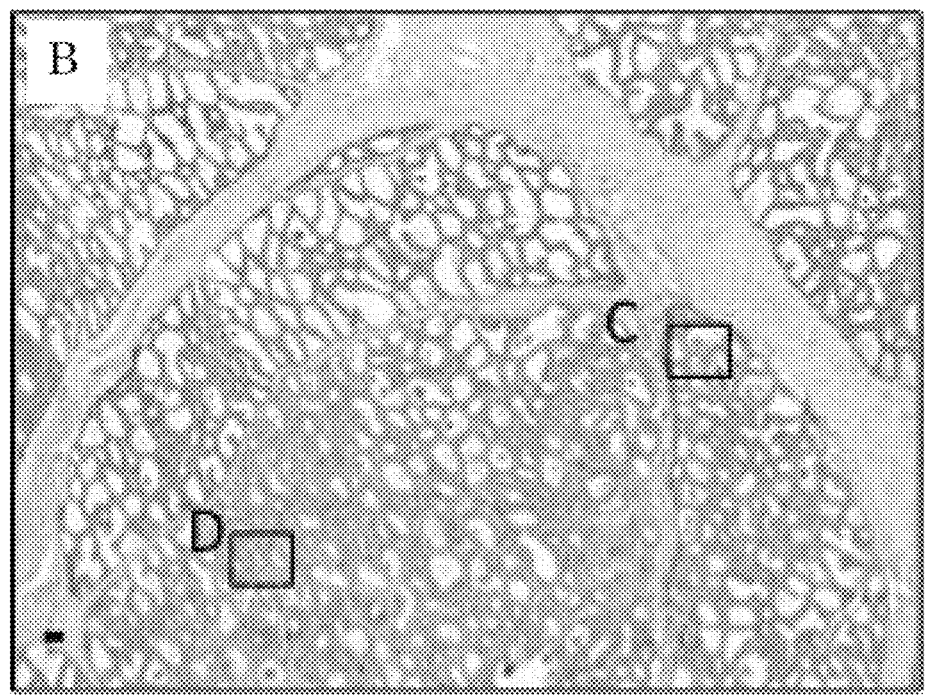
FIG. 4B is a picture illustrating localization of CyPA expression in a specimen of sliced mammary gland tissue in the mammary gland substratum prepared from a mastitis-infected cow mammary gland of an S. A administration experimental mastitis district by immuno-staining with the use of anti-CyPA (2H5-F3 antibody). The figure proves that there are sites where CyPA expression is confirmed and sites where CyPA expression is weak. The bar in FIG. 4B is 500 µm long.
Figure 4C:
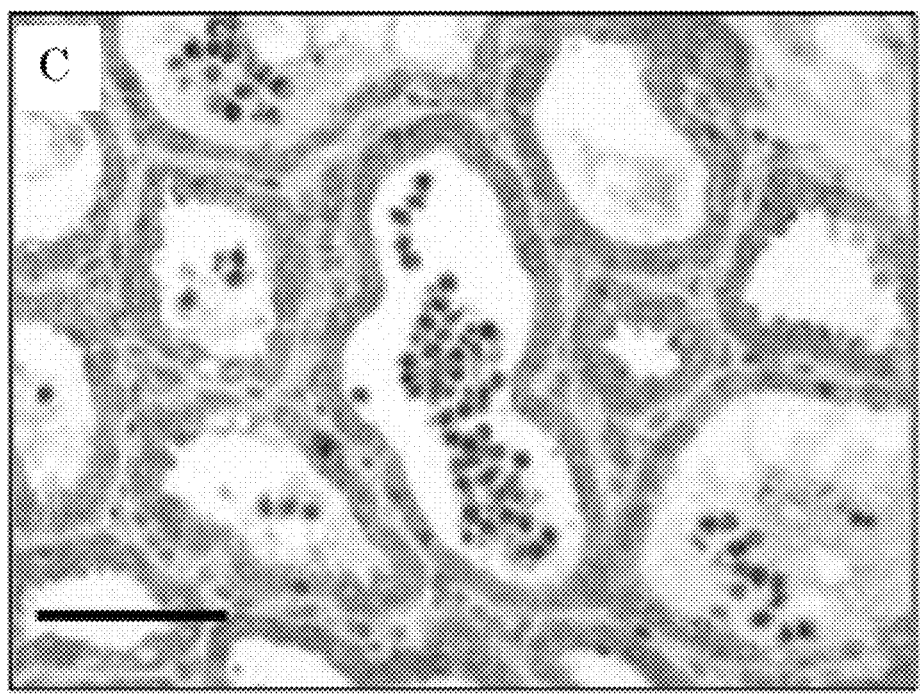
FIG. 4C is a picture illustrating localization of CyPA expression in a specimen of sliced mammary gland tissue in the mammary gland substratum prepared from a mastitis-infected cow mammary gland of an S. A administration experimental mastitis district by immuno-staining with the use of anti-CyPA (2H5-F3 antibody). The figure proves that CyPA expression is observed in mammary gland epithelial cells, in milk and at sites of in infiltrated immune cells at sites where CyPA is confirmed. The bar in FIG. 4C is 100 µm long.
Figure 4D:
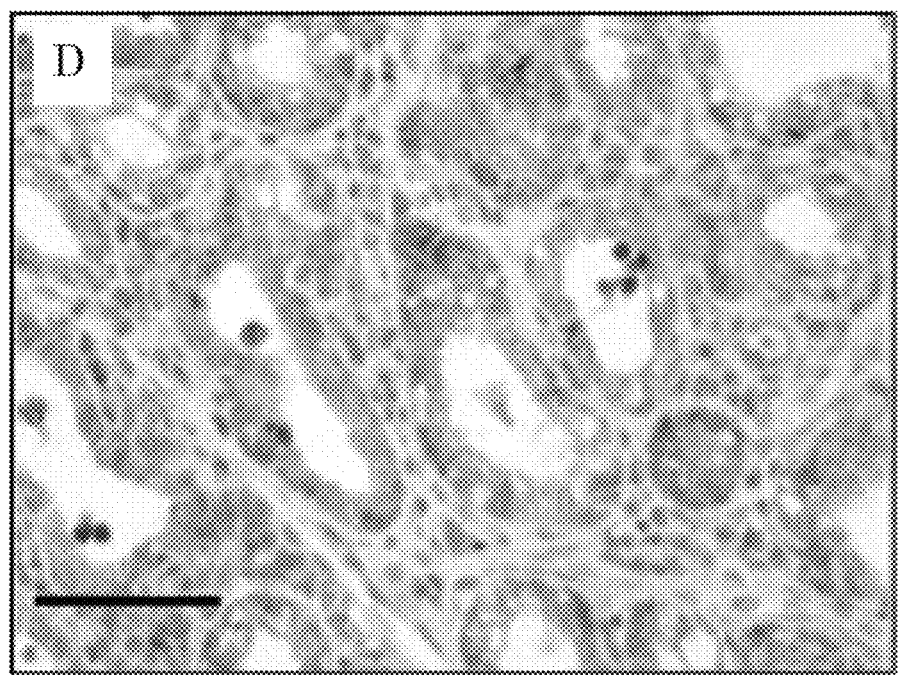
FIG. 4D is a picture illustrating localization of CyPA expression in a specimen of sliced mammary gland tissue in the mammary gland substratum prepared from a mastitis-infected cow mammary gland of an S. A administration experimental mastitis district by immuno-staining with the use of anti-CyPA (2H5-F3 antibody). The figure proves that interstitial hypertrophy and atrophy of mammary alveoli are confirmed at sites where CyPA expression is weak and that CyPA expression is slightly observed in mammary gland epithelium. The bar in FIG. 4D is 100 µm long.
Figure 5A:
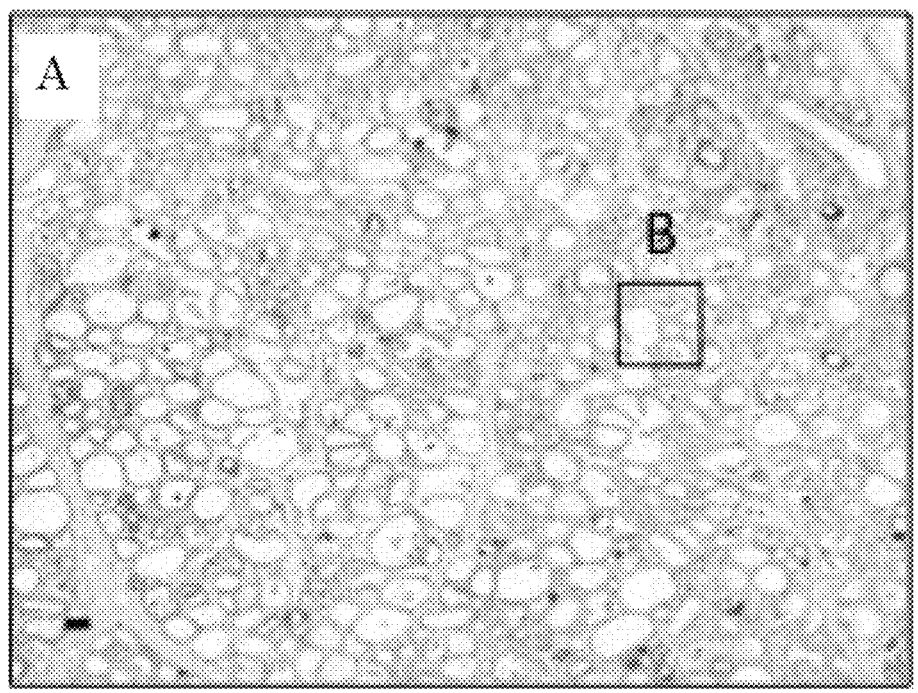
FIG. 5A is a picture illustrating localization of CyPA expression in a specimen of sliced mammary gland tissue in the mammary gland substratum prepared from a normal cow mammary gland of an Lf-administered latent mastitis district by immuno-staining with the use of anti-CyPA (2H5-F3 antibody). The figure proves that, while interstitial tissue is small and mammary alveoli are broad, there are sites of infiltrated immune cells. The bar in FIG. 5A is 500 µm long.
Figure 5B:
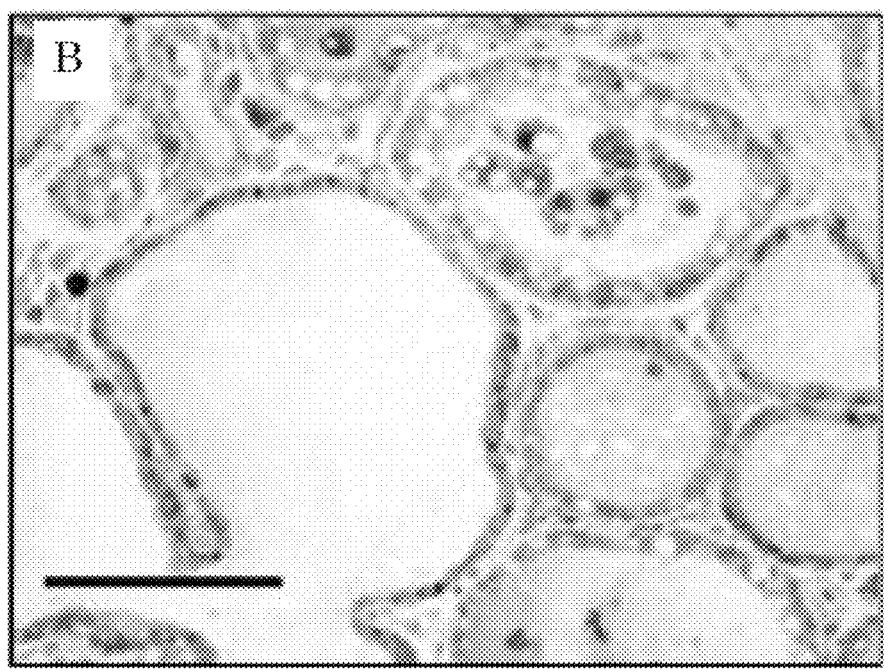
FIG. 5B is a picture illustrating localization of CyPA expression in a specimen of sliced mammary gland tissue in the mammary gland substratum prepared from a normal cow mammary gland of an Lf-administered latent mastitis district by immuno-staining with the use of anti-CyPA (2H5-F3 antibody). The figure proves that CyPA expression is weak in flat mammary gland epithelial cells and strong at sites of infiltrated immune cells and in mammary gland epithelial cells of mammary alveoli where infiltrated cells are observed. The bar in FIG. 5B is 100 µm long.

In the mammary gland tissue developing mastitis, CyPA expression stronger than the control normal mammary gland tissues was confirmed in mammary gland epithelial cells, in milk and at immune cell infiltration sites as in the mammary gland tissue developing mastitis of the SEC administration experimental district (FIGS. 4A through 4C). Additionally, in the mammary gland tissue developing mastitis of the S.A administration experimental district, interstitial hypertrophy as well as atrophied mammary alveoli and mammary epithelial cells were recognized (FIG. 4A). The inventors of the present invention presume that this phenomenon is attributable to the fact that the cows of the S.A administration experimental district were in the final milking period. Of the mammary gland tissues developing mastitis of the S.A. administration experimental district, the CyPA expression level in both the mammary alveoli and the mammary gland epithelial cells that revealed atrophy due to interstitial hypertrophy was low if compared with mammary alveoli and mammary epithelial cells that showed no atrophy (FIG. 4D).

Figure 6A:
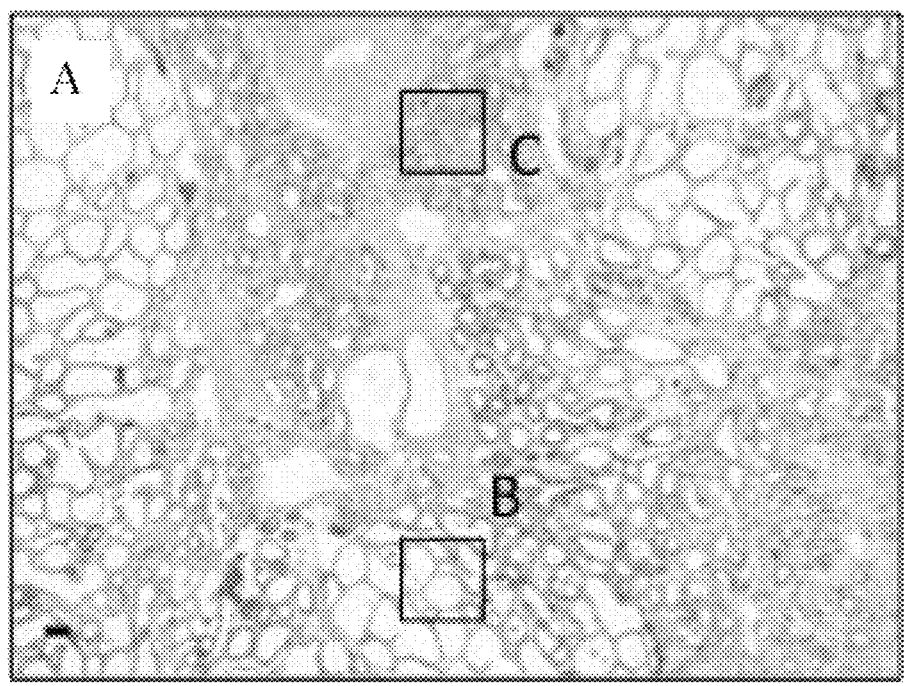
FIG. 6A is a picture illustrating localization of CyPA expression in a specimen of sliced mammary gland tissue in the mammary gland substratum prepared from a normal cow mammary gland, to which lactic acid bacteria producing peptide has been administered, by immuno-staining with the use of anti-CyPA (2H5-F3 antibody). The figure proves that there are sites showing atrophy and sites not showing atrophy in mammary alveoli. The bar in FIG. 6A is 500 µm long.
Figure 6B:
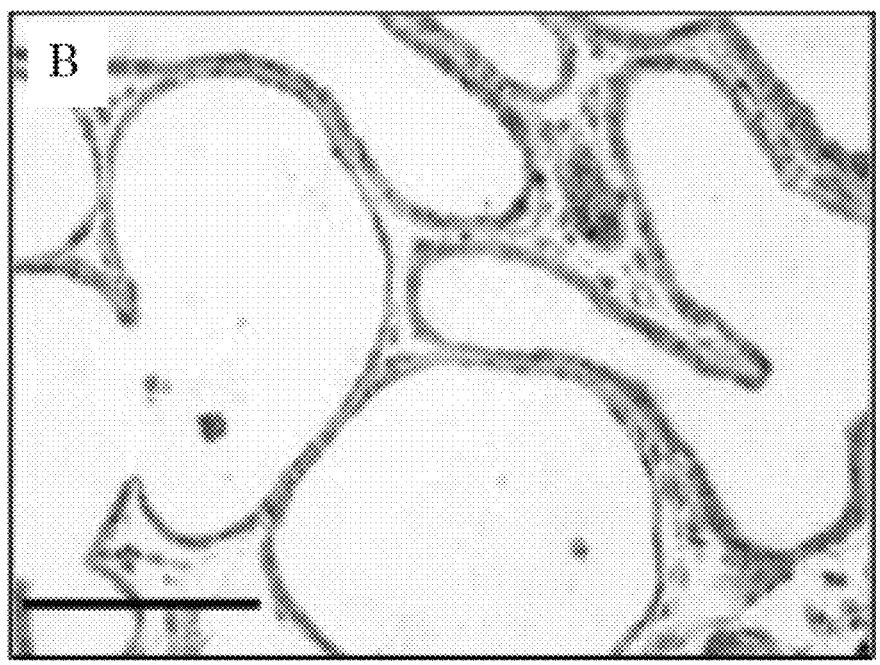
FIG. 6B is a picture illustrating localization of CyPA expression in a specimen of sliced mammary gland tissue in the mammary gland substratum prepared from a normal cow mammary gland, to which lactic acid bacteria producing peptide has been administered, by immuno-staining with the use of anti-CyPA (2H5-F3 antibody). The figure proves that CyPA expression is observed at sites where mammary alveoli are broad and interstitial tissue is small. The bar in FIG. 6B is 100 µm long.
Figure 6C:
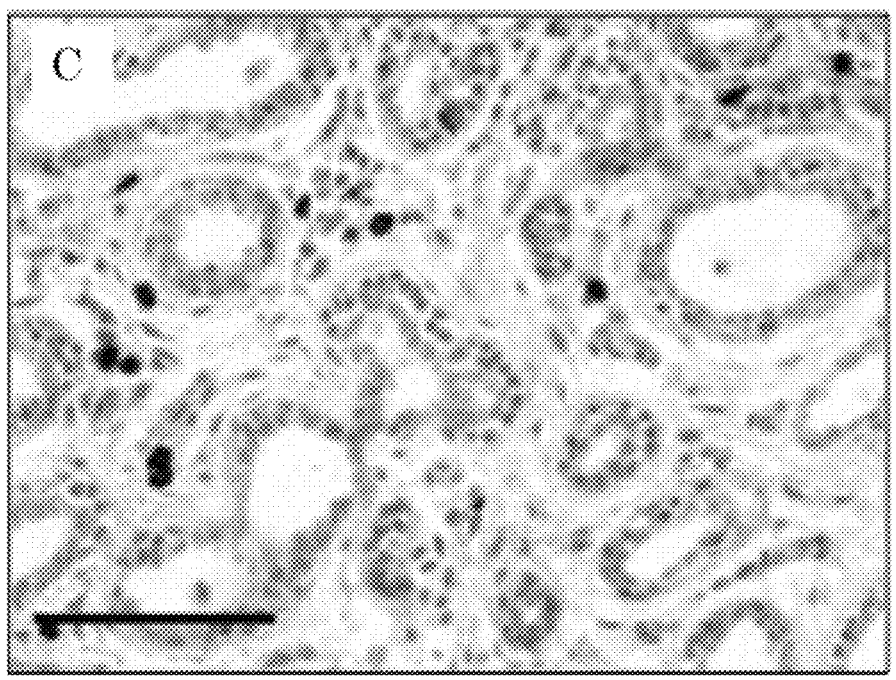
FIG. 6C is a picture illustrating localization of CyPA expression in a specimen of sliced mammary gland tissue in the mammary gland substratum prepared from a cow mammary gland, to which lactic acid bacteria producing peptide had been administered, by immuno-staining with the use of anti-CyPA (2H5-F3 antibody). The figure proves that CyPA expression is weak at sites where atrophy of mammary alveoli and interstitial hypertrophy are observed and that CyPA is strongly expressed in immune cells located in interstitial tissue. The bar in FIG. 6C is 100 µm long.
Figure 7A:
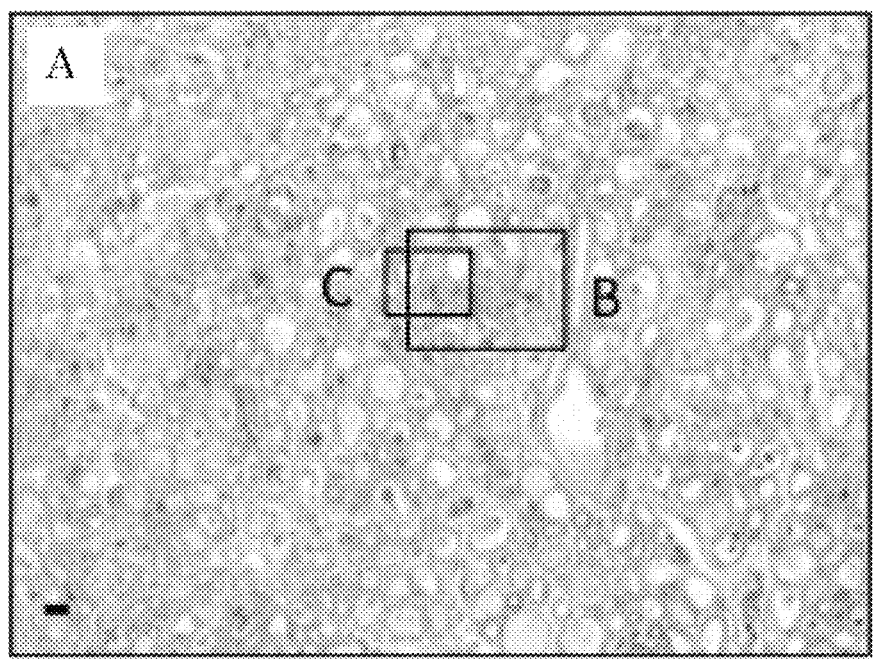
FIG. 7A is a picture illustrating localization of CyPA expression in a specimen of sliced mammary gland tissue in the mammary gland substratum prepared from a cow mammary gland, to which Lf has been administered for latent mastitis, by immuno-staining with the use of anti-CyPA (2H5-F3 antibody). The figure proves that interstitial tissue is small and mammary alveoli are broad, while there are many sites of infiltrated immune cells. The bar in FIG. 7A is 500 µm long.
Figure 7B:
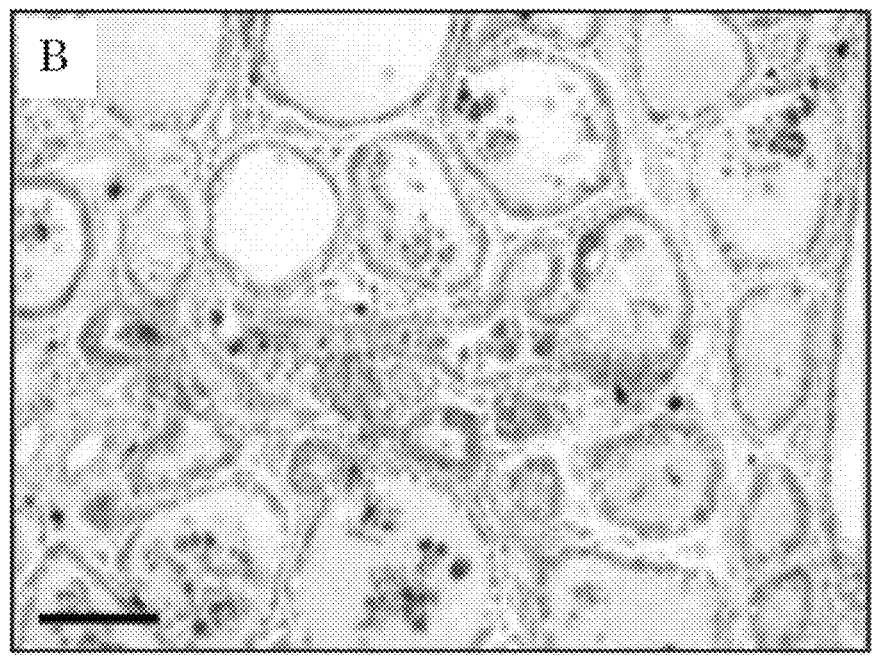
FIG. 7B is a picture illustrating localization of CyPA expression in a specimen of sliced mammary gland tissue in the mammary gland substratum prepared from a cow mammary gland, to which Lf has been administered for latent mastitis, by immuno-staining with the use of anti-CyPA (2H5-F3 antibody). The figure proves that interstitial hypertrophy is observed and the level of CyPA expression differs between sites with infiltrated immune cells and sites without infiltrated immune cells. The bar in FIG. 7B is 100 µm long.
Figure 7C:
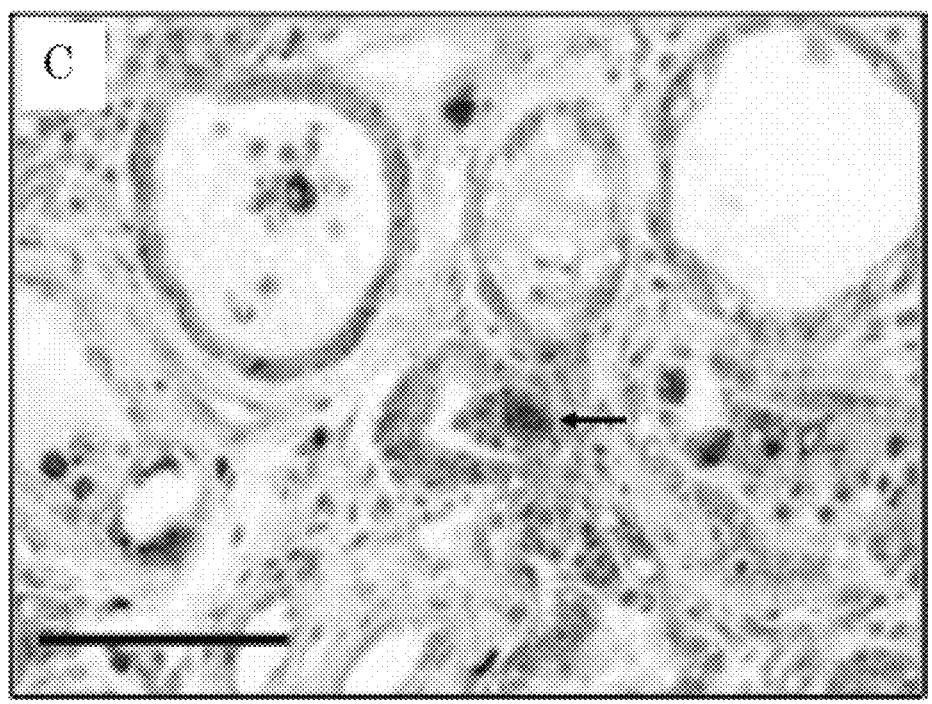
FIG. 7C is a picture illustrating localization of CyPA expression in a specimen of sliced mammary gland tissue in the mammary gland substratum prepared from a cow mammary gland, to which Lf has been administered for latent mastitis, by immuno-staining with the use of anti-CyPA (2H5-F3 antibody). The figure proves that CyPA expression is strong in mammary gland epithelial cells and deformed epithelial cells (←) where sites of infiltrated immune cells exist. The bar in FIG. 7C is 100 µm long.

(3) Observation of Mammary Gland Tissue by Lf Administration Experimental District CyPA expression in bovine mammary gland was observed by immunohistochemical staining. CyPA expression was confirmed in mammary epithelial cells and in milk of the control normal mammary gland tissues of Lf administration experimental district to which lactoferrin was administered for the purpose of treatment as in the PBS administered mammary gland tissues (control normal mammary gland tissues) of the SEC administration experimental district and those of the S. A. administration experimental district (FIGS. 5A and 5B, FIGS. 6A through 6C). The CyPA expression level of mammary alveoli and that of mammary epithelial cells which showed atrophy due to interstitial hypertrophy, were lower if compared with that of mammary alveoli and that of mammary epithelial cells which showed no atrophy, as in the mammary gland showing the onset of mastitis of the SA administration experimental district (FIG. 6C). Additionally, as for the mammary gland tissues that showed the onset of latent mastitis, a high CyPA expression level was observed in mammary epithelial cells, in milk and at immune cell infiltration sites if compared with the normal mammary gland tissues as in the above-described experimental mammary gland tissues (FIG. 7A through 7C).

3. Summary

From the above results, it was confirmed that CyPA exists in mammary epithelial cells and in milk at the mammary gland tissue collected from normal udders as intracellular protein. Similarly, CyPA expression was observed in the mammary gland tissues collected from udders that were made to show the onset of mastitis by SEC administration, which is a cytotoxin, and udders that were made to show the onset of mastitis by S. A. administration, which is a bacterium. Particularly, the CyPA expression level was high in mammary epithelial cells, in milk and at immune cell infiltration sites of mammary gland tissues developing mastitis if compared with normal mammary gland tissue. The CyPA expression level reduced in mammary alveoli and mammary epithelial cells that showed atrophy due to interstitial hypertrophy which can be observed in the final milking period and so on if compared with that in mammary alveoli and mammary epithelial cells which showed no atrophy.

2nd Analysis of Cyclophilin a Expression in Milk Originating from Mastitis-Infected Udder Quarters
1. Materials and Methods
(1) Samples Lactating Holstein cows that were being fed in Miyagi Prefecture Livestock Experiment Station were used as sample cows. A total of twelve sample cows including eight lactating Holstein cows that were diagnosed to have the onset of mastitis as a result of examination using a PL tester and CL activity and four healthy lactating Holstein cows that were free from infection history of mastitis were used. A total of 48 milk samples collected from all the udder quarters (of which an udder quarter was being treated for blind teat) were used. Table 1 shows some of the data of milk samples used in the test.

TABLE 1

| sample No. | cow No. | No. of parturitions | Days of milking | age | Udder quarter | WB No. | Milk physical properties | PL | CL ($\times 10^6$ cpm/ml) |
|---|---|---|---|---|---|---|---|---|---|
| 1 | 14 | 4 | 81 | 5 years | Front right | 1 | | | 0.037 |
| | | | | | Rear right | 2 | | Agglomer . . . 2+ color 2+ | 96.090 |
| | | | | | Front left | 3 | | | 0.033 |
| | | | | | Rear left | 4 | | | 0.023 |
| 2 | 69 | 5 | 102 | 7 years 9 months | Front right | 5 | | | 0.076 |
| | | | | | Rear right | 6 | | | 0.100 |
| | | | | | Front left | 7 | | | 7.740 |
| | | | | | Rear left | 8 | Clots/flakes found | Agglomer . . . 3+ color + | 73.220 |
| 3 | 81 | 5 | 46 | 6 years 8 months | Front right | 9 | Clots/flakes found | Agglomer . . . 3+ color 2+ | 668.900 |
| | | | | | Rear right | 10 | | | 0.056 |
| | | | | | Front left | 11 | Viscous/clots/flakes found | | 0.040 |
| | | | | | Rear left | 12 | | | 0.035 |
| 4 | 107 | 2 | 16 | 2 years 1 month | Front right | 13 | Highly viscous | Agglomer . . . 3+ color 2+ | 26.890 |
| | | | | | Rear right | 14 | Highly viscous | | 1.817 |
| | | | | | Front left | 15 | Highly viscous | Agglomer . . . 2+ color + | 188.900 |
| | | | | | Rear left | 16 | Highly viscous | | 0.290 |
| 5 | 34 | 3 | 255 | 4 years 3 months | Front right | 17 | Clots/flakes found/highly viscous | | 418.500 |
| | | | | | Rear right | 18 | | | 0.292 |
| | | | | | Front left | 19 | Blind teat | | |
| | | | | | Rear left | 20 | | | 0.255 |
| 6 | 38 | 1 | 18 | 2 years 7 moths | Front right | 21 | | | 0.677 |
| | | | | | Rear right | 22 | | | 0.118 |
| | | | | | Front left | 23 | Highly viscous | Agglomer . . . 3+ color 2+ | 610.600 |
| | | | | | Rear left | 24 | | | 0.103 |
| 7 | 69 | 5 | 155 | 7 years 10 months | Front right | 25 | | | 0.249 |
| | | | | | Rear right | 26 | | | 0.376 |
| | | | | | Front left | 27 | Viscous to some degree | Agglomer . . . 3+ color 3+ | 54.030 |
| | | | | | Rear left | 28 | Viscous to some degree | Agglomer . . . 3+ color 3+ | 45.660 |

TABLE 1-continued

| sample No. | cow No. | No. of parturitions | Days of milking | age | Udder quarter | WB No. | Milk physical properties | PL | CL (×10⁶) cpm/ml |
|---|---|---|---|---|---|---|---|---|---|
| 8 | 67 | 2 | 84 | 3 years 12 months | Front right | 29 | | | 0.971 |
| | | | | | Rear right | 30 | | | 1.226 |
| | | | | | Front left | 31 | Clots/flakes found | | 1.297 |
| | | | | | Rear left | 32 | Clots/flakes found | | 2.584 |
| 9 | 96 | 1 | 29 | 3 years 5 months | Front right | 33 | Many clots/flakes found | Agglomer . . . 3+ color 2+ | 0.049 |
| | | | | | Rear right | 34 | | | 0.096 |
| | | | | | Front left | 35 | | | 0.085 |
| | | | | | Rear left | 36 | | | 0.091 |
| 10 | 103 | 1 | 23 | 2 years 7 months | Front right | 37 | Clots/flakes Found | | 3.016 |
| | | | | | Rear right | 38 | | | 0.283 |
| | | | | | Front left | 39 | | | 0.221 |
| | | | | | Rear left | 40 | | | 0.291 |
| 11 | 108 | 1 | 50 | 2 years | Front right | 41 | | | 0.309 |
| | | | | | Rear right | 42 | | | 0.233 |
| | | | | | Front left | 43 | | | 0.228 |
| | | | | | Rear left | 44 | | | 0.282 |
| 12 | 906 | 1 | 18 | 2 years 1 month | Front right | 45 | Clotty and flaky | | 0.148 |
| | | | | | Rear right | 46 | | | 0.094 |
| | | | | | Front left | 47 | Clotty and flaky | | 0.124 |
| | | | | | Rear left | 48 | | | 0.124 |

(2) Reagents

Anti-CyPA antibody (rabbit-anti human CyPA: Abcam (registered trademark)), which is commercially available polyclonal antibody, was used for CyPA analysis by Western blotting.

(3) Method of Detecting CyPA Protein in Whey by Western Blotting

A. Extraction and Quantification of Whey Protein in Milk Samples

Whey protein in each milk sample was extracted and quantified by the following procedure. The milk sample was subjected to a centrifugation process at 1,100G and at 4° C. for 20 minutes. After the process, butterfat and precipitations were removed from the milk sample and whey was collected. The collected whey was incubated at 37° C. for 30 minutes by Pierce (registered trademark) BCA Protein Assay Kit (Thermo Sientific). The protein concentration of the incubated whey was measured by DS PHARMA BIOMEDICAL to obtain a result of quantification of 14 µg/µl.

B. Western Blotting

After the protein quantification, the whey sample was analyzed for CyPA protein by the following procedure.

(A) Method of not Adding Mercaptoethanol: Non-Reducing Treatment

On the 1st day, after the protein quantification, the protein in the whey sample was isolated by SDS-PAGE, using PAGEL (ATTO; E-T520L) so as to make the protein concentration equal to 21 µg/lane. The isolated protein was transferred onto Immobion-P Transfer membranes (Millipore), using the membranes and ceramide Lai system (Bio-Rad) at 1.2 mA/cm² for 60 minutes. After the transfer operation, the membranes were washed three times with TBS-Tween (0.1% Tween20/TBS; TBS-T) for 10 minutes. The washed membranes were incubated with a blocking process for 60 minutes (3% normal goat serum/TBS-T). After the blocking process, the membranes were washed three times with TBS-Tween for 10 minutes. The washed membranes were incubated with a primary antibody at 4° C. for 14 hours (diluted 1:1000 in anti-CyPA antibody/TBS-T).

On the 2nd day, the membranes that were subjected to the reaction were washed with TBS-Teen for 10 minutes for a total of three times. The washed membranes were then incubated with a secondary antibody at room temperature for 60 minutes by alkaline phosphatase coupled goat-anti rabbit IgG (ZYMED). After the reaction, the membranes were washed three times with TBS-Tween for 10 minutes. The washed membranes were further washed with TBS for 5 minutes. The washed membranes were subjected to a color development process at room temperature for 5 minutes by ECF substrate dilution buffer (BD Healthcare). After the color development, bands were detected from the membranes by Molecular Imager FX (Bio Rad).

(B) Method of Adding 2ME; Reducing Treatment

On the 1st day, the protein in the whey sample adding 5% 2ME after the protein quantification was isolated by means of SDS-PAGE using PAGEL (ATTO; E-T520L) so as to make the protein concentration equal to 21 μg/lane. The isolated protein was transferred onto Immobion-P Transfer membranes (Millipore), using the membranes and ceramide Lai system (Bio-Rad) at 1.2 mA/cm$^2$ for 60 minutes. After the transfer operation, the membranes were washed three times with TBS-Tween (0.1% Tween20/TBS; TBS-T) for 10 minutes. The washed membranes were incubated with blocking process for 60 minutes (3% normal goat serum/TBS-T). After the blocking process, the membranes were washed three times with TBS-Tween for 10 minutes. The washed membranes were incubated with a primary antibody reaction at 4° C. for 14 hours (diluted 1:1000 in anti-CyPA antibody/TBS-T).

On the 2nd day, the membranes were washed three times with TBS-Tween for 10 minutes. The washed membranes were then incubated with secondary antibody reaction at room temperature for 60 minutes by alkaline phosphatase coupled goat-anti rabbit IgG (ZYMED). After the reaction, the membranes were washed three times with TBS-Tween for 10 minutes. The washed membranes were further washed with TBS for 5 minutes. The washed membranes were subjected to a color development process at room temperature for 5 minutes by ECF substrate dilution buffer (BD Healthcare). After the color development process, bands were detected from the membranes by means of Molecular Imager FX (Bio Rad).

C. Coomassie Brilliant Blue (CBB) Staining

The protein in each of the whey samples that had been subjected to protein quantification was analyzed by following the procedure. The protein in the whey sample was isolated by SDS-PAGE, using PAGEL (ATTO; E-T520L), as to make the protein concentration equal to 21 μg/lane. The gel after the isolation process was then washed three times with MQ for 5 minutes. The washed gel was then subjected to a color development process at room temperature for 20 minutes by means of ULTRA-FAST Coomassie Stain (NRV, USA). After the color development process, bands were detected from the gel.

(4) Measurement of CyPA Expression Intensity

The protein in the whey sample was isolated by following the above procedure of (3) B (B). Bands were detected and imaged from the gel after the isolation process by Molecular Imager FX. The obtained image file as a result of the imaging was turned into a black and white reversed image file by Photshop 5.0 LE, using a grey scale. The obtained image file by reversing black and white was analyzed by gel plotting Macros of NIH Imager Ver. 1.62. USA and the band intensity was measured. The obtained CyPA concentration by measuring the band intensity was converted into a numerical form by using the milk sample (analysis No. 42) of the rear right udder quarter of the cow No. 108 in Table 1 as reference. Additionally, the correlation between the obtained CyPA concentration and the CL value was analyzed.

2. Results (1) Establishment of a Method of Detecting CyPA in Milk

Figure 8:
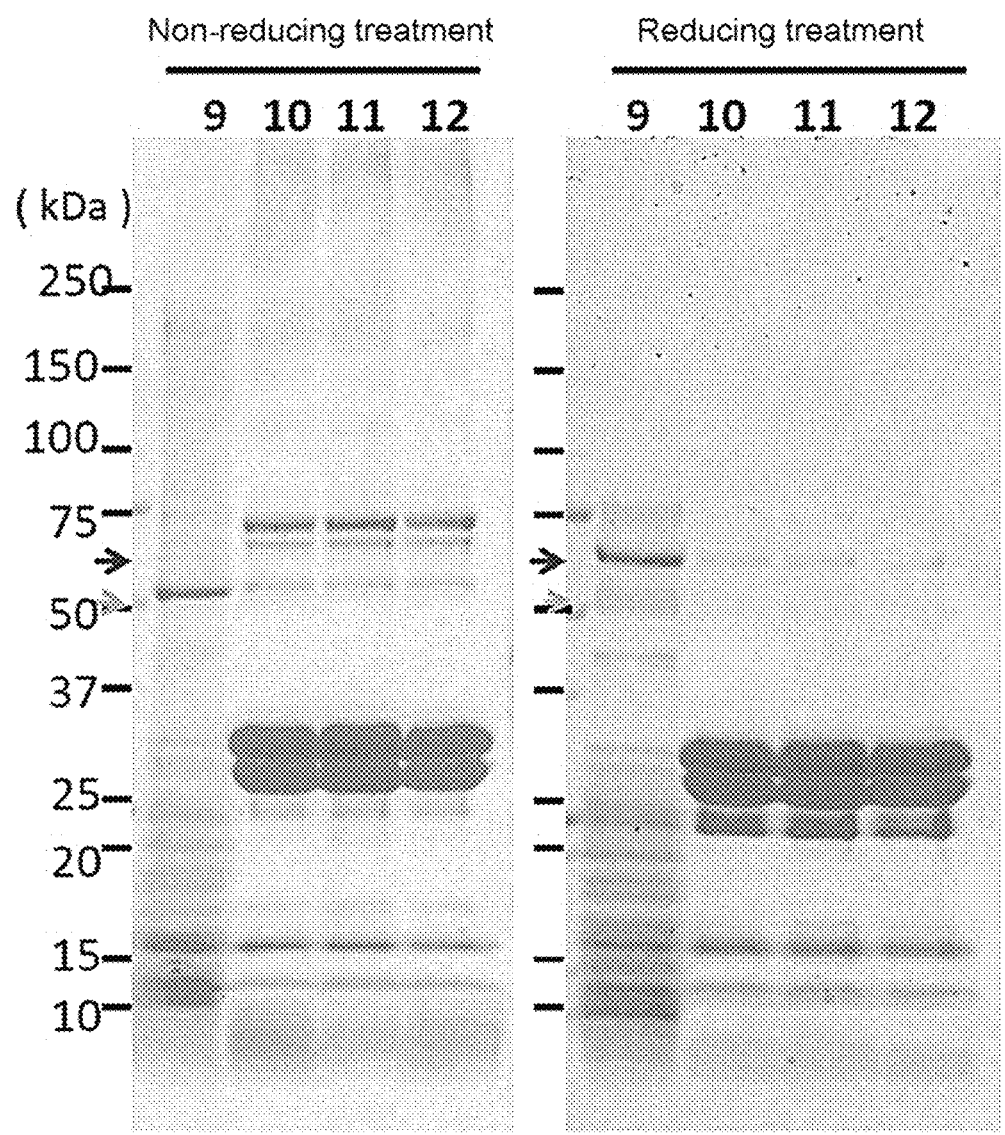
FIG. 8 is an illustration of the results of CBB staining of proteins in whey obtained from cow body No. 81 shown in Table 1, showing the difference between the use of a reducing treatment and that of a non-reducing treatment.

The milk samples (analysis Nos. 9 through 12) of udder quarters of the cow No. 81 were analyzed for protein. As a result of Coomassie Brilliant Blue (CBB) staining, a band was detected around 65 kDa from the analysis of non-infected udder quarter milk samples (analysis Nos. 10 through 12) that had been subjected to a reducing treatment and a mastitis developing udder quarter milk sample (analysis No. 9) (FIG. 8). It is assumed that this band is a band resulting from reduction of IgG of originally about 160 kDa. The protein of around 50 kDa found as a result of the non-reducing treatment was not detected after the reducing treatment.

Figure 9A:
FIG. 9A is an illustration of the results of analysis of CyPA proteins in whey by Western blotting, using specimens of cow body No. 81 in Table 1, to show the difference between the use of a reducing treatment and the use of a non-reducing treatment. The figure proves that no non-specific reaction due to secondary antibody takes place regardless of the use or non-use of reducing treatment when no anti-CyPA antibody is employed.
Figure 9B:
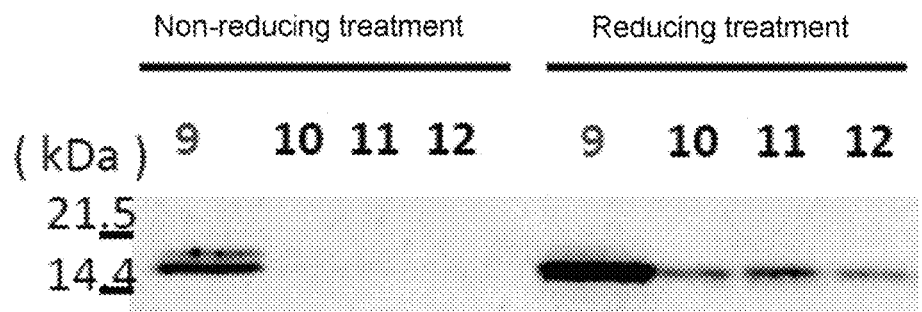
FIG. 9B is an illustration of the results of analysis of CyPA proteins in whey by Western blotting, using specimens of cow body No. 81 in Table 1, to show the difference between the use of a reducing treatment and the use of a non-reducing treatment. The figure proves that, when a non-reducing treatment is used, CyPA can be detected only in analysis No. 9 for a inflammatory udder quarter whereas, when a reducing treatment is used, CyPA is detected inmost of the milk samples but the CyPA content level is very high in analysis No. 9 for a inflammatory udder quarter.

Protein analysis was conducted by means of Western blotting. Regardless of non-reducing treatment and reducing treatment, no non-specific reaction to CyPA in milk samples by secondary antibody was observed. As a result of non-reducing treatment, CyPA was detected in mastitis developing udder quarter milk sample (analysis No. 9) (FIGS. 9A and 9B). However, no CyPA was detected in the other non-infected udder quarter milk samples (analysis Nos. 10 through 12). On the other hand, CyPA was detected in mastitis developing udder quarter milk sample and non-infected udder quarter milk samples that had been subjected to a reducing treatment and the band intensity of the mastitis developing udder quarter milk sample (analysis No. 9) was relatively very high. Therefore, it was found that CyPA in milk samples can be detected by executing a reducing treatment.

(2) Analysis of CyPA Expression in Milk Samples

Figure 10A:
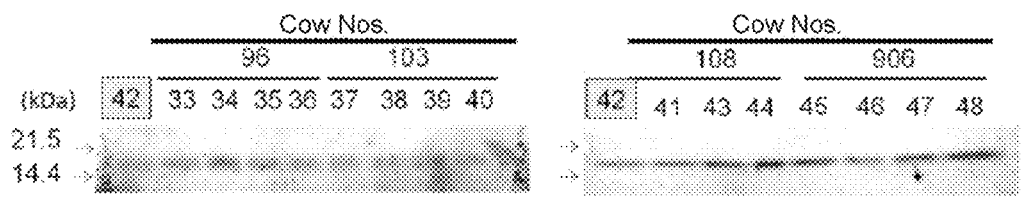
FIG. 10A is an illustration of the results of protein analysis for CyPA in milk by means of Western blotting after conducting a reducing treatment on the milk samples of analysis Nos. 1 through 48 (including blind teat sample 19). The figure proves that CyPA expression could be confirmed in the milk collected from healthy cow udder quarters (analysis Nos. 33 through 48).
Figure 10B:
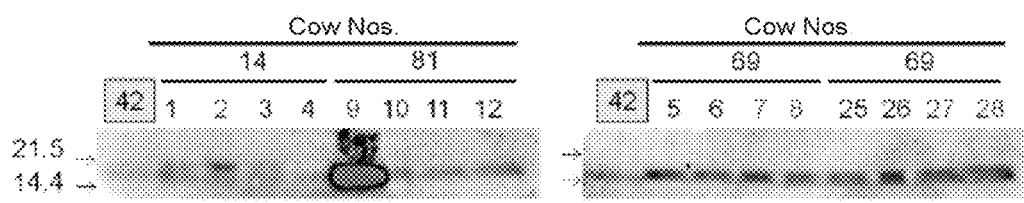
FIG. 10B is an illustration of the results of protein analysis for CyPA in milk by means of Western blotting after conducting a reducing treatment on the milk samples of analysis Nos. 1 through 48 (including blind teat sample 19). The figure proves that the CyPA expression level in the milk collected from udder quarters showing the onset of mastitis is higher if compared with the CyPA expression level in the milk collected from healthy cow udder quarters (analysis Nos. 33 through 48) shown in FIG. 10A.
Figure 10C:
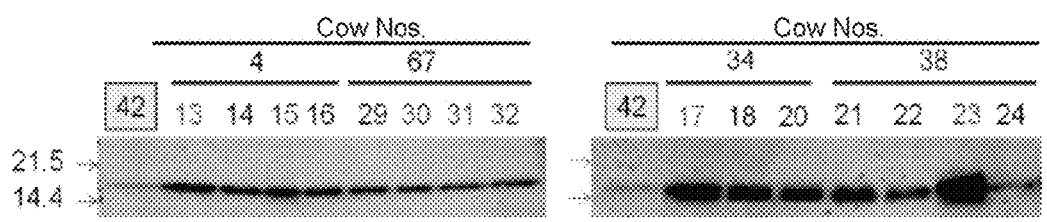
FIG. 10C is an illustration of the results of protein analysis for CyPA in milk by means of Western blotting after conducting a reducing treatment on the milk samples of analysis Nos. 1 through 48 (including blind teat sample 19). The figure proves that the CyPA expression level in the milk collected from udder quarters showing the onset of mastitis is higher if compared with the CyPA expression level in the milk collected from healthy cow udder quarters (analysis Nos. 33 through 48) shown in FIG. 10A.

On the basis of the fact that CyPA protein was detected in milk samples originating from mastitis-infected milk secreting cows as described in (1) above, all the milk samples (analysis Nos. 1 through 48, of which analysis No. 19 is being subjected to a blind teat treatment) were subjected to a reducing treatment and the CyPA protein in the obtained whey samples was analyzed. CyPA protein was detected as a result of the analysis using healthy cow udder quarter milk samples (analysis Nos. 33 through 48) and mastitis developing udder quarter milk samples (analysis Nos. 1 through 32) (FIGS. 10A through 10C). The quantity of CyPA protein was small in healthy cow udder quarter milk if compared with mastitis developing udder quarter milk. On the other hand, the quantity of CyPA protein in each of the non-infected udder quarter milk samples of mastitis developing cows (analysis No. 1, 3-6, 10-12, 14, 16, 18-22, 24-26, 29) was smaller than the quantity of CyPA protein in each of the mastitis developing udder quarter milk samples (analysis No. 2, 7-9, 13, 15, 17, 23, 27, 28, 30-32).

TABLE 2

Milk Samples from Miyagi Prefecture Livestock Experiment Station

| Udder quarter | Analysis No. | Protein content (μg/μl) | Milk physical properties | PL | CL (×10$^6$ cpm/ml) | CyPA relative values |
|---|---|---|---|---|---|---|
| Front right | 1 | 21.9 | | | 0.037 | 4.90 |
| Rear right | 2 | 25.5 | | Agglomeration 2+ color 2+ | 96.090 | 6.78 |
| Front left | 3 | 24.0 | | | 0.033 | 6.38 |
| Rear left | 4 | 33.0 | | | 0.023 | 0.98 |
| Front right | 5 | 14.3 | | | 0.076 | 4.31 |
| Rear right | 6 | 14.1 | | | 0.100 | 3.23 |

TABLE 2-continued

Milk Samples from Miyagi Prefecture Livestock Experiment Station

| Udder quarter | Analysis No. | Protein content (μg/μl) | Milk physical properties | PL | CL (×10$^6$ cpm/ml) | CyPA relative values |
|---|---|---|---|---|---|---|
| Front left | 7 | 18.3 | | | 7.740 | 4.75 |
| Rear left | 8 | 20.1 | Clots and flakes found | Agglomeration 3+ color + | 73.220 | 4.04 |
| Front right | 9 | 31.2 | Clots and flakes found | Agglomeration 3+ color 2+ | 668.900 | 66.15 |
| Rear right | 10 | 27.6 | | | 0.056 | 4.34 |
| Front left | 11 | 25.8 | Viscous/clots and flakes found | | 0.040 | 3.20 |
| Rear left | 12 | 27.3 | | | 0.035 | 6.40 |
| Front right | 13 | 17.9 | Highly viscous | Agglomeration 3+ color 2+ | 26.890 | 18.94 |
| Rear right | 14 | 23.4 | Highly viscous | | 1.817 | 8.98 |
| Front left | 15 | 20.8 | Highly viscous | Agglomeration 2+ color + | 188.900 | 14.36 |
| Rear left | 16 | 21.4 | Highly viscous | | 0.290 | 11.15 |
| Front right | 17 | 37.1 | Clots and flakes found/highly viscous | | 418.500 | 61.50 |
| Rear right | 18 | 32.1 | | | 0.292 | 21.47 |
| Front left | 19 | | Blind teat | | | |
| Rear left | 20 | 33.8 | | | 0.255 | 17.53 |
| Front right | 21 | 31.5 | | | 0.677 | 33.45 |
| Rear right | 22 | 34.6 | | | 0.118 | 11.86 |
| Front left | 23 | 36.8 | Highly viscous | Agglomeration 3+ color 2+ | 610.600 | 47.80 |
| Rear left | 24 | 31.3 | | | 0.103 | 5.07 |
| Front right | 25 | 33.0 | | | 0.249 | 4.00 |
| Rear right | 26 | 30.4 | | | 0.376 | 7.38 |
| Front left | 27 | 33.2 | Viscous to some degree | Agglomeration 3+ color 3+ | 54.030 | 4.97 |
| Rear left | 28 | 32.0 | Viscous to some degree | Agglomeration 3+ color 3+ | 45.660 | 11.59 |
| Front right | 29 | 31.8 | | | 0.971 | 10.09 |
| Rear right | 30 | 34.5 | | | 1.226 | 9.07 |
| Front left | 31 | 37.3 | Clots and flakes found | | 1.297 | 6.89 |
| Rear left | 32 | 38.2 | Clots and flakes found | | 2.584 | 12.46 |
| Front right | 33 | 32.0 | Many clots and flakes found | Agglomeration 3+ color 2+ | 0.049 | 1.20 |
| Rear right | 34 | 24.1 | | | 0.096 | 2.25 |
| Front left | 35 | 32.7 | | | 0.085 | 1.57 |
| Rear left | 36 | 34.9 | | | 0.091 | 0.94 |
| Front right | 37 | 34.2 | Clots and flakes found | | 3.016 | 1.37 |
| Rear right | 38 | 30.3 | | | 0.283 | 1.32 |
| Front left | 39 | 29.9 | | | 0.221 | 1.54 |
| Rear left | 40 | 33.8 | | | 0.291 | 0.86 |
| Front right | 41 | 41.1 | | | 0.309 | 0.67 |
| Rear right | 42 | 37.8 | | | 0.233 | 1.00 |
| Front left | 43 | 36.7 | | | 0.228 | 1.17 |
| Rear left | 44 | 39.9 | | | 0.282 | 1.42 |
| Front right | 45 | 27.0 | Clotty and flaky | | 0.148 | 1.55 |
| Rear right | 46 | 28.6 | | | 0.094 | 0.72 |
| Front left | 47 | 28.2 | Clotty and flaky | | 0.124 | 1.36 |
| Rear left | 48 | 26.3 | | | 0.124 | 1.15 |

(3) Correlation Between CyPA and CL Activity in Milk Sample

The CyPA expression intensities of all the milk samples were measured by using the milk sample of analysis No. 42 of cow body No. 108 as reference that showed lower values in terms of milk physical properties, PL test and CL activity among the udder quarter milk samples of the healthy cows. The relative values of CyPA expressions of analysis Nos. 1 through 48 (of which analysis No. 19 was being treated for blind teat) were computationally determined (Table 2). Correlation was observed between the CL activities and the respective corresponding CyPA expression intensities ($p<0.0001$) (FIG. 11). It became clear that, as the CL activity rises, the CyPA expression intensity increases.

3. Summary

As a result of Western blotting of the whey samples that were subjected to a non-reducing treatment, no CyPA was detected in the non-infected udder quarter milk samples. However, CyPA was detected to a large extent from the mastitis developing udder quarter milk samples that showed a high CL activity. On the other hand, as a result of a reducing treatment of whey protein, CyPA was detected in the whey of the milk samples originating from healthy cows and the milk samples originating from mastitis developing cows.

As a result of Western blotting analysis of CyPA expressions with the use of all the milk samples that were subjected to a reducing treatment, CyPA protein was detected from the udder quarter milk samples originating from healthy cows with no previous history of mastitis (analysis Nos. 33-48), the non-infected udder quarter milk samples originating from mastitis developing cows (analysis Nos. 1, 3-6, 10-12, 14, 16, 18-22, 24-26, 29) and the mastitis developing udder quarter milk samples (analysis Nos. 2, 8, 9, 13, 15, 18, 27, 28, 32). CyPA protein was detected to a small extent in the healthy cow udder quarter milk samples when compared with the non-infected udder quarter milk samples of mastitis developing cows and the mastitis developing udder quarter milk samples. CyPA protein was detected to a small extent in the non-infected udder quarter milk samples of mastitis developing cows when compared with the mastitis developing udder quarter milk samples. The quantity of CyPA protein was detected to a very large extent in the udder quarter milk samples that were positive in the PL test and showed a high CL activity level (analysis Nos. 2, 8, 9, 13, 15, 18, 27, 28, 32). The findings described above agree with the tendency of CyPA expression intensity in mammary epithelial cells and in mammary alveoli in normal mammary gland tissues and in mastitis developing mammary gland tissues.

It has been shown that, as the CL activity rises, the CyPA protein content in the milk samples increases. Thus, the correlation between mastitis and an increase of CyPA expression was proved. From the regression line, it was found that the CyPA expression intensity was 5.5 when the CL value was $1 \times 10^4$ cpm/ml (FIG. 11). It is defined that a cow udder that secretes milk showing a CL activity level of not less than $1 \times 10^6$ cpm/ml is infected by mastitis. Udder quarter milk samples showing a CL activity level of less than $1 \times 10^6$ cpm/ml and a CyPA expression intensity of not lower than 5.5 existed (analysis Nos. 1, 3, 12, 16, 18, 20-22,26). The CyPA expression intensity level of these udder quarter milk samples was higher than the CyPA expression intensity level of healthy cow udder quarter milk samples. Furthermore, as the CL values of some milk samples (analysis Nos. 1, 3, 12, 16, 18, 20-22, 26) were higher than the CL values of the milk samples of the udder quarters that were diagnosed to develop mastitis as a result of PL test (analysis Nos. 8, 27), there is a probability that those milk samples were collected from udder quarters that were in initial stages of mastitis. In fact, the onset of mastitis of the udder quarter from which the milk sample having the analysis No. 26 was collected was confirmed later.

The invention claimed is:

1. A method of identifying and treating a site infected by latent mastitis in a subject comprising:
    detecting cyclophilin A in the milk collected from an udder or an udder quarter of the subject with an anti-cyclophilin A antibody bound to and immobilized on an insoluble carrier and thereby determining the cyclophilin A level in the milk;
    determining the onset of latent mastitis in the udder or the udder quarter of the subject on the basis of the cyclophilin A level in the milk as the cyclophilin A level in the milk is higher than the cyclophilin A level in the milk collected from a healthy udder or udder quarter; and
    administering an antibiotic agent, cytokines, and/or natural substances showing anti-bacterial effects to a subject infected with latent mastitis.

2. The method according to claim 1, wherein determining the onset of latent mastitis in the udder or the udder quarter requires the cyclophilin A level in the milk is twice or more than twice as higher than the cyclophilin A level in the milk collected from a healthy udder or udder quarter.

3. The method according to claim 1, wherein the anti-cyclophilin A antibody is bound to beads and immobilized thereon.

* * * * *

SEQUENCE LISTING

<160> NUMBER OF SEQ ID NOS: 8

<210> SEQ ID NO 1
<211> LENGTH: 159
<212> TYPE: PRT
<213> ORGANISM: Bos taurus

<400> SEQUENCE: 1

```
Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Ile Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Asp Asp Glu Asn Phe Ile Leu Lys Phe Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Leu Trp Gln Gly Glu Arg Gly His Glu Tyr Cys Gly Ser His Gly Ala
    130                 135                 140

Leu Trp Val Gln Glu Trp Gln Asp Gly Gln Glu Asp His His Cys
145                 150                 155
```

<210> SEQ ID NO 2
<211> LENGTH: 112
<212> TYPE: PRT
<213> ORGANISM: Ovis aries

<400> SEQUENCE: 2

```
Ala Leu Ser Thr Gln Glu Lys Gly Phe Gly Thr Lys Gln Ser Cys Phe
1               5                   10                  15
```

```
His Arg Ile Ile Pro Gly Phe Met Cys Gln Gly Gly Asp Phe Thr Arg
            20                  25                  30

His Asn Gly Thr Gly Lys Ser Ile Tyr Gly Glu Lys Phe Asp Asp
        35                  40                  45

Glu Asn Phe Ile Leu Lys His Thr Gly Pro Gly Ile Leu Ser Met Ala
 50                  55                  60

Asn Ala Gly Pro Asn Thr Asn Gly Ser Gln Phe Phe Ile Cys Thr Ala
 65                  70                  75                  80

Lys Thr Glu Trp Leu Asp Gly Lys His Val Val Phe Gly Lys Val Lys
                 85                  90                  95

Glu Gly Met Asn Ile Val Glu Ala Met Glu Arg Phe Gly Ser Arg Asn
            100                 105                 110
```

<210> SEQ ID NO 3
<211> LENGTH: 164
<212> TYPE: PRT
<213> ORGANISM: Mus musculus

<400> SEQUENCE: 3

```
Met Val Asn Pro Thr Val Phe Phe Asp Ile Thr Ala Asp Asp Glu Pro
 1               5                  10                  15

Leu Gly Arg Val Ser Phe Glu Leu Phe Ala Asp Lys Val Pro Lys Thr
                20                  25                  30

Ala Glu Asn Phe Arg Ala Ile Ser Thr Gly Glu Lys Gly Phe Gly Tyr
            35                  40                  45

Lys Gly Ser Ser Phe His Arg Ile Ile Pro Gly Phe Met Cys Gln Gly
 50                  55                  60

Gly Asp Phe Thr Arg His Asn Gly Thr Gly Gly Arg Ser Ile Tyr Gly
 65                  70                  75                  80

Glu Lys Phe Asp Asp Glu Asn Phe Ile Leu Lys Phe Thr Gly Pro Gly
                 85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ser Asp
145                 150                 155                 160

Cys Gly Gln Leu
```

<210> SEQ ID NO 4
<211> LENGTH: 165
<212> TYPE: PRT
<213> ORGANISM: Macaca mulatta

<400> SEQUENCE: 4

```
Met Val Asn Pro Thr Val Phe Phe Asp Ile Ala Val Asp Gly Glu Pro
 1               5                  10                  15

Leu Gly Arg Val Ser Phe Glu Leu Phe Ala Asp Lys Val Pro Lys Thr
                20                  25                  30

Ala Glu Asn Phe Arg Ala Ile Ser Thr Gly Glu Lys Gly Phe Gly Tyr
            35                  40                  45

Lys Gly Ser Cys Phe His Arg Ile Ile Pro Gly Phe Met Cys Gln Gly
 50                  55                  60
```

Gly Asp Phe Thr Arg His Asn Gly Thr Gly Lys Ser Ile Tyr Gly
65                  70                  75                  80

Glu Lys Phe Asp Asp Glu Asn Phe Ile Leu Lys Phe Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
            115                 120                 125

Phe Gly Lys Val Lys Glu Gly Met Asn Ile Val Glu Ala Met Glu Arg
            130                 135                 140

Phe Gly Ser Arg Asn Gly Lys Thr Ser Lys Lys Ile Thr Ile Ala Asp
145                 150                 155                 160

Cys Gly Gln Leu Glu
            165

<210> SEQ ID NO 5
<211> LENGTH: 165
<212> TYPE: PRT
<213> ORGANISM: Pan troglodytes

<400> SEQUENCE: 5

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Ile Ser Thr Gly Glu Lys Gly Phe Gly Tyr
        35                  40                  45

Lys Gly Ser Cys Phe His Arg Ile Ile Pro Gly Phe Met Cys Gln Gly
50                  55                  60

Gly Asp Phe Thr Arg His Asn Gly Thr Gly Lys Ser Ile Tyr Gly
65                  70                  75                  80

Glu Lys Phe Asp Asp Glu Asn Phe Ile Leu Lys Phe Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
            115                 120                 125

Phe Gly Lys Val Lys Glu Gly Met Asn Ile Val Glu Ala Met Glu Arg
            130                 135                 140

Phe Gly Ser Arg Asn Gly Lys Thr Ser Lys Lys Ile Thr Ile Ala Asp
145                 150                 155                 160

Cys Gly Gln Leu Glu
            165

<210> SEQ ID NO 6
<211> LENGTH: 164
<212> TYPE: PRT
<213> ORGANISM: Rattus norvegicus

<400> SEQUENCE: 6

Met Val Asn Pro Thr Val Phe Phe Asp Ile Thr Ala Asp Asp Glu Pro
1               5                   10                  15

Leu Gly Arg Val Cys Phe Glu Leu Phe Ala Asp Lys Val Pro Lys Thr
            20                  25                  30

Ala Glu Asn Phe Arg Ala Ile Ser Thr Gly Glu Lys Gly Phe Gly Tyr
        35                  40                  45

-continued

Lys Gly Ser Ser Phe His Arg Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Asp Asp Glu Asn Phe Ile Leu Lys Phe Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Ser Ile Val Glu Ala Met Glu Arg
    130                 135                 140

Phe Gly Ser Arg Asn Gly Lys Thr Ser Lys Lys Ile Thr Ile Ser Asp
145                 150                 155                 160

Cys Gly Gln Leu

<210> SEQ ID NO 7
<211> LENGTH: 165
<212> TYPE: PRT
<213> ORGANISM: Pongo abelii

<400> SEQUENCE: 7

Met Val Asn Pro Thr Val Phe Leu Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Ile Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Asp Asp Glu Asn Phe Ile Leu Lys Phe Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 8
<211> LENGTH: 165
<212> TYPE: PRT
<213> ORGANISM: Homo sapiens

<400> SEQUENCE: 8

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Ile Ser Thr Gly Glu Lys Gly Phe Gly Tyr

-continued

```
            35                  40                  45
Lys Gly Ser Cys Phe His Arg Ile Ile Pro Gly Phe Met Cys Gln Gly
    50                  55                  60

Gly Asp Phe Thr Arg His Asn Gly Thr Gly Gly Lys Ser Ile Tyr Gly
65                  70                  75                  80

Glu Lys Phe Asp Asp Glu Asn Phe Ile Leu Lys Phe Thr Gly Pro Gly
            85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
            115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
            165
```